United States Patent
Yates-Binder et al.

(10) Patent No.: US 8,734,775 B2
(45) Date of Patent: May 27, 2014

(54) CHEMOKINE DERIVED PEPTIDES THAT BIND WITH CHEMOKINE RECEPTOR CXCR3 AND USES FOR CHRONIC WOUND AND ANGIOGENESIS INHIBITION TREATMENTS

(75) Inventors: Cecelia C. Yates-Binder, Pittsburgh, PA (US); Jesse Jaynes, Auburn, AL (US); Timothy Turner, Auburn, AL (US); Alan Wells, Pittsburgh, PA (US); Richard J. Bodnar, Pittsburgh, PA (US)

(73) Assignees: University of Pittsburgh, Pittsburgh, PA (US); Tuskegee University, Tuskegee, AL (US)

( * ) Notice: Subject to any disclaimer, the term of this patent is extended or adjusted under 35 U.S.C. 154(b) by 0 days.

(21) Appl. No.: 13/219,375

(22) Filed: Aug. 26, 2011

(65) Prior Publication Data
US 2013/0053319 A1 Feb. 28, 2013

(51) Int. Cl.
*A61K 38/19* (2006.01)
*A61K 45/00* (2006.01)
*C07K 14/435* (2006.01)

(52) U.S. Cl.
USPC ....... 424/85.2; 514/13.3; 514/19.2; 514/19.3; 530/326; 530/351

(58) Field of Classification Search
None
See application file for complete search history.

(56) References Cited

U.S. PATENT DOCUMENTS 5,994,292 A * 11/1999 Tosato et al. .......... 514/9.1

OTHER PUBLICATIONS

Wells, 1990, Biochemistry 29:8509-8517.*
Bork, Genome Research 2000, 10:398-400.*
Skolnick et al., Trends in Biotech, 2000, 18(1):34-39.*
Tokuriki and Tawflik, Current Opinion in Structural Biology; 2009, 19: 596-604.*
Doerks et al., 1998, Trends in Genetics 14:248-250.*
Sato et al, British Journal of Cancer; 2007, vol. 96, pp. 1735-1739.*
Jennifer H. Cox, et al., "Matrix Metalloproteinase Processing of CXCL11/I-TAC Results in Loss of Chemoattractant Activity and Altered Glycosaminoglycan Binding," The Journal of Biological Chemistry, vol. 283, No. 28, pp. 19389-19399, Jul. 11, 2008.
Elizabeth D. Feldman, et al., Interferon y-Inducible Protein 10 Selectively Inhibits Proliferation and Induces Apoptosis in Endothelial Cells, Annals of Surgical Oncology, 13(1), pp. 125-133, 2006.
Laura Lasagni, et al., "An Alternatively Spliced Variant of CXCR3 Mediates the Inhibition of Endothelial Cell Growth Induced by IP-10, MIG, and I-TAC, and Acts As Functional Receptor for Platelet Factor 4," The Journal of Experimental Medicine, vol. 197, No. 11, Jun. 2, 2003 pp. 1537-1549.
G, Jawahar Swaminathan, et al., "Crystal Structures of Oligomeric Forms of the IP-10/CXCL 10 Chemokine," Structure, vol. 11, pp. 521-532, May 2003.

* cited by examiner

*Primary Examiner* — Bridget E Bunner
*Assistant Examiner* — Fozia Hamud
(74) *Attorney, Agent, or Firm* — Hogan Lovells US LLP

(57) ABSTRACT

Disclosed are peptides having activity against receptor CXCR3 are disclosed that exhibit activity in preventing the formation of new vessels and activity in mediating the dissociation of newly-formed vessels and resolving of wounds in the later stages of wound healing. Preferred peptides are derived from the α-helix portion IP-10 (CXCL10) or from IP-9 (CXCL11), are nontoxic, and smaller than naturally occurring peptides, making them useful in therapies against diseases or disease states marked by unwanted angiogenesis, including tumorogenic diseases such as cancers, and in healing of chronic wounds.

4 Claims, 16 Drawing Sheets
(2 of 16 Drawing Sheet(s) Filed in Color)

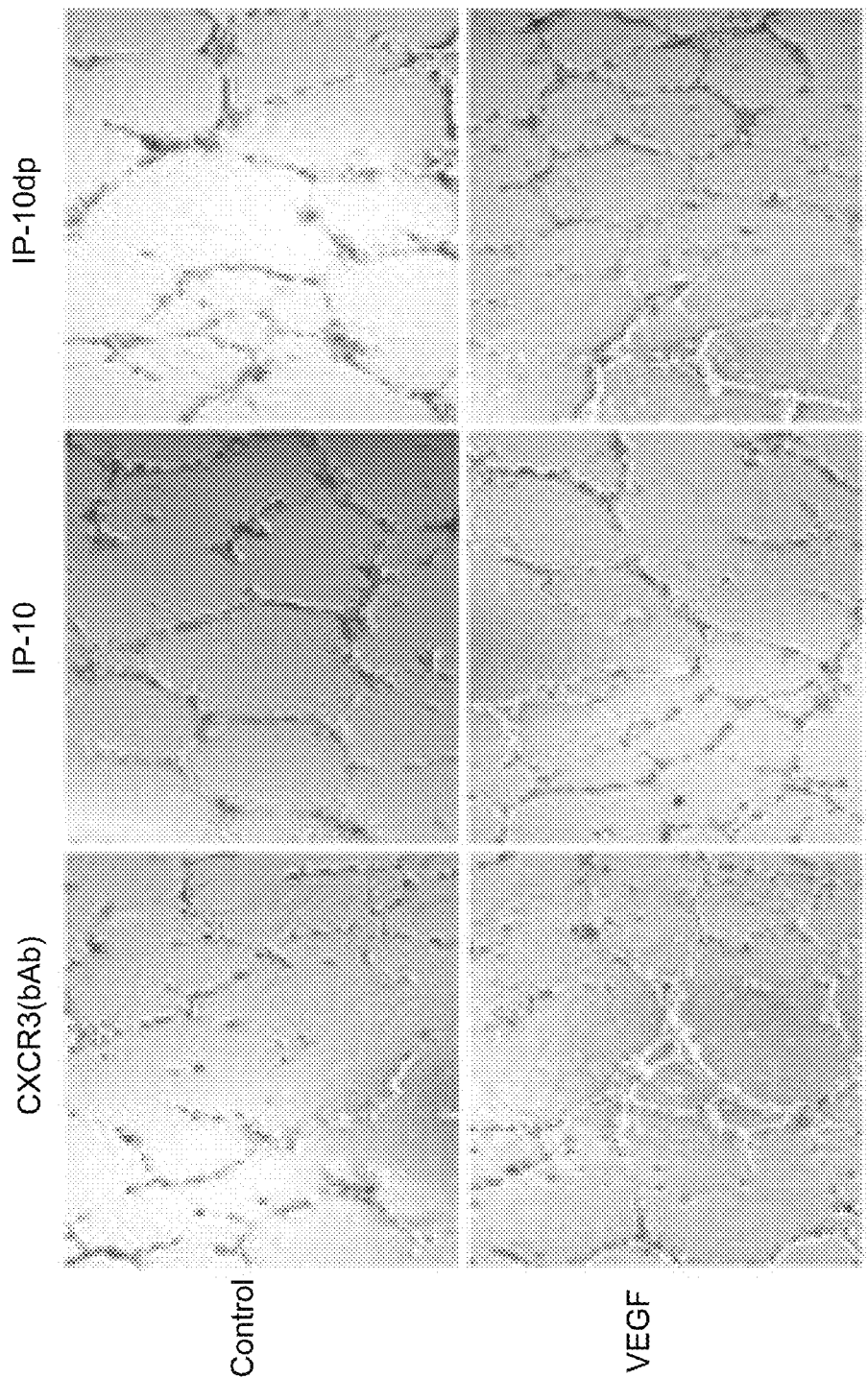

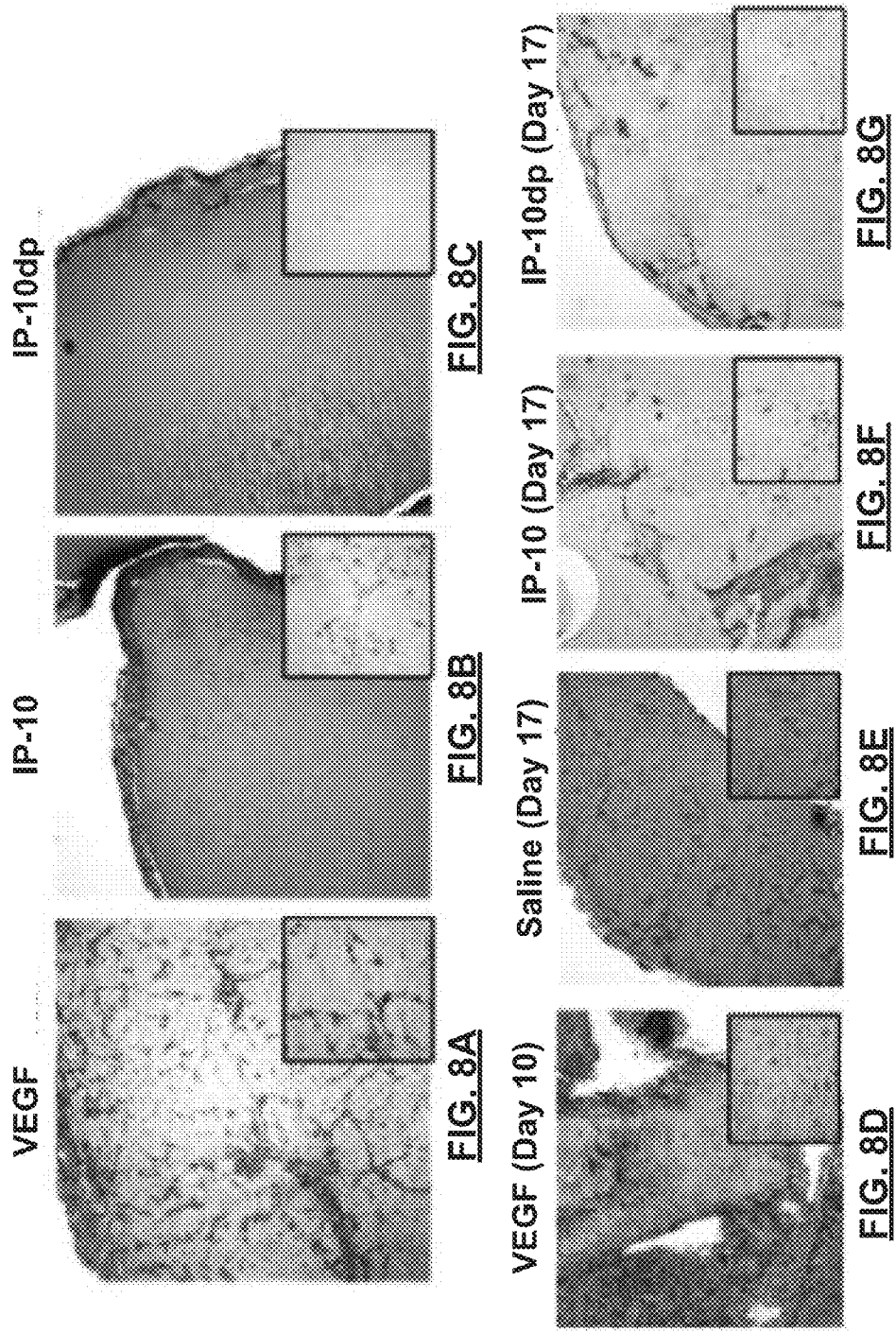

SEQUENCE LISTING

<160> NUMBER OF SEQ ID NOS: 5

<210> SEQ ID NO 1
<211> LENGTH: 22
<212> TYPE: PRT
<213> ORGANISM: Homo sapiens

```
<220> FEATURE:
<223> OTHER INFORMATION: IP-10dp

<400> SEQUENCE: 1

Pro Glu Ser Lys Ala Ile Lys Asn Leu Leu Lys Ala Val Ser Lys Glu
1               5                   10                  15

Met Ser Lys Arg Ser Pro
            20

<210> SEQ ID NO 2
<211> LENGTH: 77
<212> TYPE: PRT
<213> ORGANISM: Homo sapiens
<220> FEATURE:
<223> OTHER INFORMATION: IP-10

<400> SEQUENCE: 2

Val Pro Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
            20                  25                  30

Ser Gln Phe Ser Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Met Ser Lys Arg Ser Pro
65                  70                  75

<210> SEQ ID NO 3
<211> LENGTH: 94
<212> TYPE: PRT
<213> ORGANISM: Homo sapiens
<220> FEATURE:
<223> OTHER INFORMATION: IP-9

<400> SEQUENCE: 3

Met Ser Val Lys Gly Met Ala Ile Ala Leu Ala Val Ile Leu Cys Ala
1               5                   10                  15

Thr Val Val Gln Gly Phe Pro Met Phe Lys Arg Gly Arg Cys Leu Cys
            20                  25                  30

Ile Gly Pro Gly Val Lys Ala Val Lys Val Ala Asp Ile Glu Lys Ala
        35                  40                  45

Ser Ile Met Tyr Pro Ser Asn Asn Cys Asp Lys Ile Glu Val Ile Ile
    50                  55                  60

Thr Leu Lys Glu Asn Lys Gly Gln Arg Cys Leu Asn Pro Lys Ser Lys
65                  70                  75                  80

Gln Ala Arg Leu Ile Ile Lys Lys Val Glu Arg Lys Asn Phe
                85                  90

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
catatgaagt cctggaaaag gg                                            22

<210> SEQ ID NO 5
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
acaactacac cctggtcatc a                                               21
```

US 8,734,775 B2

CHEMOKINE DERIVED PEPTIDES THAT BIND WITH CHEMOKINE RECEPTOR CXCR3 AND USES FOR CHRONIC WOUND AND ANGIOGENESIS INHIBITION TREATMENTS

STATEMENT REGARDING FEDERALLY SPONSORED RESEARCH OR DEVELOPMENT

This invention was made with government support under 1 U54 CA118623-01, RO1GM063569, and RO1GM069668, all awarded by the NIH. The government has certain rights in the invention.

SEQUENCE LISTING

The instant application contains a Sequence Listing which has been submitted in ASCII format via EFS-Web and is hereby incorporated by reference in its entirety. Said ASCII copy, created on Apr. 4, 2013, is named 057193-00017_SL.txt and is 2,808 bytes in size.

FIELD OF THE INVENTION

The present invention relates to peptides having angiogenesis inhibition activity that may be useful in treating diseases associated with excessive angiogenesis, including tumorogeneic diseases such cancers, genes for encoding the same, and methods and uses thereof in the treatment of such diseases. More particularly, the present invention relates to peptides that target tumor cells, including cancerous cells, which peptides comprise a portion derived from Interferon gamma-induced protein 10, genes for encoding the same, and methods and uses thereof in the treatment of diseases associated with such tumors, including cancers.

BACKGROUND OF THE INVENTION

Generally in the biomedical arts, angiogenesis refers to the process of formation of new blood vessels from pre-existing ones (e.g., an existing monolayer of endothelial cells sprouting to form capillaries), whereas vasculogenesis is the term used for the formation of new blood vessels when there are no pre-existing ones (e.g., by a de novo production of endothelial cells). Angiogenesis plays a critical role in biologic processes such as organ development, wound healing, and tumor growth. It requires a well-orchestrated integration of soluble and matrix factors and timely recognition of such signals to regulate this process. Vasculogenesis plays a significant role during embryologic development, but can also occur in the adult organism. Circulating endothelial progenitor cells (derivatives of stem cells) can contribute to varying degrees to neo-vascularization during the early stages of tumor growth or in revascularization healing processes process following trauma (e.g., after cardiac ischemia). Thus, angiogenesis and vasculogenesis are critical for several normal and healthy physiological processes including embryogenesis, organogenesis and vascular remodeling. For ease of reference herein, both angiogenesis and vasculogenesis will collectively be referred to hereinafter as angiogenesis, and any reference to angiongenesis or use of words derived therefrom (e.g., "angiogenic," "angiostatic," etc.) should be interpreted in this collective fashion unless stated otherwise.

Angiogenesis, however, also is a fundamental step in the transition of tumors from a dormant state to a malignant one. Tumors are believed to induce blood vessel angiogenesis by secreting various growth factors (e.g., VEGF or bFGF), and/ or by reducing the production of anti-growth factor enzymes (e.g., PKG). Such growth factors can induce capillary growth into the tumor, which research suggests helps supply the required nutrients that allow for tumor expansion and/or transports away waste products formed by rapidly dividing tumor cells. Angiogenesis thus is believed to be a key step for the transition from a small and harmless cluster of abnormal cells to a large tumor. Angiogenesis is also linked with the spread of a tumor, or metastasis. Single cancer cells can break away from an established solid tumor, enter the blood vessel, and be carried to a distant site, where those cells can implant and begin the growth of a secondary tumor. The subsequent growth of such metastases into secondary tumors will likewise require a supply of nutrients and oxygen and a waste disposal pathway—again implicating angiogenesis. Research has thus proceeded into the use of angiogenesis inhibitors in cancer treatments.

The angiogenesis process is regulated by a complex and interrelated system of pathways that involve various angiogenic and angiostatic factors. An imbalance of the angiogenic process can result in over or under expression of angiogenic or angiostatic factors, resulting in tumor vascularization and growth, or untimely termination of the angiogenesis process, resulting in unhealed chronic wounds.

Chemokines are a family of small proteins secreted by cells, which generally function as chemo-attractants, such as to guide the migration of cells. Members of the chemokine family are divided into four groups depending on the spacing of their first two cysteine residues. For example, the commonly used nomenclature in the art for referring to chemokine peptides having two adjacent cysteines near its amino terminus (or β-chemokine) is as a "CC-family" chemokine. As such, the name CCL1 would be used to denote the ligand 1 of the CC-family of chemokines, and the name CCR1 would be used to denote the receptor for CCL1. Likewise, the CXC-family of chemokines are a-chemokines, having their two N-terminal cysteines being separated by one amino acid, represented conventionally in its name with an "X," and the ligands and receptors are represented using a similar CXCL# and CXCR# nomenclature.

Recent evidence demonstrates that members of the CXC chemokine family can act as either angiogenic or angiostatic factors, depending upon the presence of the ELR (Glu-Leu-Arg) motif in their $NH_2$ terminus (see Strieter, R M et al., 1995, "The functional role of the ELR motif in CXC chemokine-mediated angiogenesis," J. Biol. Chem. 270: 27348-57). Among the small CXC-family of chemokines are CXCL10 (also known as Interferon gamma-induced protein 10 or simply IP-10), CXCL11 (also known as IP-9/ITAC), and CXCL9 (Mig), which all lack the canonical N-terminal ELR sequence (see Godessart, N, et al., 2001, "Chemokines in autoimmune disease," Curr. Opin. Immunol. 6: 670-675). These secreted proteins bind in common to the ubiquitous CXCR3 chemokine receptor, which is a seven transmembrane G-protein receptor that exists as two isoforms (CXCR3-A and CXCR3-B), which isoforms regulate chemotaxis and proliferation in a various cells types and acts as an angiostatic agent in endothelial cells (see Kelsen, S G et al., 2004, "The chemokine receptor CXCR3 and its splice variant are expressed in human airway epithelial cells," Am. J. Physiol. Lung Cell Mol. Physiol. 287: L584-591). The A-isoform pf CXCLR3 has been found to be stimulatory, inducing both migration and proliferation, while the B-isoform inhibits migration and proliferation (see Lasagni, L. et al., 2003, "An alternatively spliced variant of CXCR3 mediates the inhibition of endothelial cell growth induced by IP-10, Mig, and I-TAC, and acts as functional receptor for platelet factor 4," J. Exp. Med.

197:1537-1549; Bodnar, R J et al., 2006, "IP-10 blocks vascular endothelial growth factor-induced endothelial cell motility and tube formation via inhibition of calpain," Circ. Res. 98:617-625; and Bodnar et al., 2009, "IP-10 induces dissociation of newly formed blood vessels," J. Cell. Sci. 122:2064-2077). It has been proposed that CXCR3-A promotes chemotaxis and cell proliferation and CXCR3-B stimulates signals for growth inhibition (see Aidoudi, S et al., 2010, "Interaction of PF4 (CXCL4) with the vasculature: A role in atherosclerosis and angiogenesis," Thromb. Haemost. 104: 941-948). Recent reports suggest that CXCR3 signaling results in chemotactic activation of keratinocytes via a PLCβ pathway that induces μ-calpain activation, which is mediated by calcium influx. In endothelial cells, however, chemotaxis is blocked via the inhibition of μ-calpain by a cAMP-PKA mediated pathway (see Bodnar, 2006, supra). Therefore, it is suggested that the regulation of these very different cellular responses is due to CXCR3-A/B binding of chemokines.

Furthermore, among the CXC-family of chemokines, CXCL10 specifically has been reported to be angiostatic and have antitumor activity via its signaling through CXCR3; resulting in inhibition of angiogenesis induced by vascular endothelial growth factor ("VEGF") and basic fibroblast growth factor ("bFGF"), and in eventual in vitro and in vivo regression of nascent vessels (see Addison, C L et al., 2009, "The CXC chemokine receptor 2, CXCR2, is the putative receptor for ELR+ CXC chemokine-induced angiogenic activity," J. Immunol. 165: 5269-5277; Bodnar, 2006, supra; and Bodnar, 2009, supra). In particular, newly forming vessels express CXC receptor 3 ("CXCR3"), and that activation of CXCR3 by its ligand CXCL10 both inhibits development of new vasculature and causes regression of newly formed vessels. CXCL10 is atypical, however, in that it specifically activates a single receptor (CXCR3) yet in several cells types induces motility while in others inhibit it (see Satish, L et al., 2005, "Interferon-inducible protein 9 (CXCL11)-induced cell motility in keratinocytes requires calcium flux-dependent activation of μ-calpain," Mol. Cell. Biol. 5:1922-1941; Yates, C C et al., 2007, "Delayed and deficient dermal maturation in mice lacking the CXCR3 ELR-negative CXC chemokine receptor," Am. J. Pathol. 1701: 484-495). For example, it has been reported that the CXCR3-binding chemokine CXCL10 can limit new vessel growth by inhibiting endothelial cell migration (see Bodnar, 2006, supra). In contrast, CXCL10 does not block the motility of keratinocytes but rather it increases their motility (see Yates, 2007, supra). Evidence suggests that this modulation occurs via the activation of two separate downstream pathways of CXCR3 (see Yates, C C et al., 2009, "Delayed reepithelialization and basement membrane regeneration after wounding in mice lacking CXCR3," Wound Repair Regen. 17:34-41; Yates, C C et al., 2008, "ELR-negative CXC chemokine CXCL11 (IP-9/I-TAC) facilitates dermal and epidermal maturation during wound repair," Am. J. Pathol. 173: 643-652; and Bodnar, 2006, supra]. CXCR3 thus is a part of a family of chemokine receptors that have opposing effects, and targeting one over the other can lead to regulation of specific cells or even cellular function in whole. There is an imperfect understanding in the art regarding exactly how and why CXCL10 and peptides derived therefrom may be used as a therapeutic, because the CXCL10 ligand binding to a single receptor can induce different biological effects.

CXCL10 is secreted by a diverse spectrum of tissues displaying pleiotrophic effects in immunity, angiogenesis, and organ-specific metastases of cancer, making it a promising therapeutic target for a wide variety of diseases. CXCL10 and CXCL11 also are known to be present in dermal wounds during the late transition from the regenerative to the resolving phase of wound healing. Specifically, CXCL11/IP-9 is expressed from re-differentiating basal keratinocytes behind the leading edge of a wound (see Satish et al., 2003, "ELR-negative CXC chemokine IP-9 as a mediator of epidermal-dermal communication during wound repair," Journal of Investigative Dermatology, 120, 1110-1117), and CXCL-10/IP-10 is produced in the late healing state dermis where it is produced by endothelial cells (see Luster, et al., 1995, "The IP-10 chemokine binds to a specific cell surface heparan sulfate site shared with platelet factor 4 and inhibits endothelial cell proliferation." Journal of Experimental Medicine, 182(1), 219-231). The timing and expression of IP-9 and IP-10, along with their cellular affects, has been determined by Applicants to provide a key communication between the dermis and epidermis during wound repair that, at least in part, signals an end to the regenerative phase and initiation of the remodeling phase of wound repair.

It has previously been determined that CXCL10 consists of three anti-parallel sheets overlayed by a helix at the C-terminus (see Swaminathan, G J et al., 2003, "Crystal structures of oligomeric forms of the IP-10/CXCL10 chemokine," Structure 11: 521-532). It has been suggested that the N-loop region of the sheets play a role in binding of the protein to the receptor (see Clark-Lewis, I et al., 2003, "Structure-function relationship between the human chemokine receptor CXCR3 and its ligands," J. Biol. Chem. 278:289-95), but the domain responsible receptor-activation has not been previously characterized such that it is fully understood.

To develop CXCL10 as a therapeutic agent, and, in particular, new and superior therapeutic peptides derived from CXCL10, structural details of its mechanism of action are needed to understand its role in the aforementioned pathological conditions. Further understanding of CXCL10 would potentially permit new peptides to be derived from the functional domain of CXCL10 that is responsible for CXCR3-B activation and related inhibition of endothelial cell function.

Thus, there remains a need in the art for improved therapeutics for the inhibition of angiogenesis that are highly effective in promoting cancer remission, preventing tumor malignancy and metastases, and in preventing progression of the disease to more advanced and aggressive stages.

SUMMARY OF THE INVENTION

In light of the above needs, it is an object of the present invention to identify peptides having potency associated with receptor CXCR3.

Furthermore, it is an object of the present invention to provide new treatments for patients with tumorogenic diseases, including cancers such as prostate and breast cancer, and for patients with chronic wounds.

Additionally, it is an object of one or more embodiments of the present invention to provide treatment formulations that are highly effective while being non-toxic.

The various embodiments of the present invention achieve these and other objects via compounds that exhibit wound healing and angiogenesis inhibition activity associated with CXCR3, and which are useful to treat patients suffering from chronic wounds or to prevent tumor formation or metastases, such as that associated with cancers such as breast cancer. Certain preferred peptides according to the invention derive from a 21 amino acid fragment of IP-10 comprising residues 78-98 and constituting the -helical domain of that protein, which was identified and synthesized by Applicants. This peptide fragment is referred to herein as IP-10dp, for IP-10 derived peptide, and has the sequence SEQ ID NO: 1. The sequence for full length IP-10 is reproduced below as SEQ ID NO: 2.

Peptide IP-10dp has the ability to modulate endothelial cell function in a manner consistent with inhibiting angiogenesis. In particular, IP-10dp inhibits endothelial cell motility and vessel formation, and induces vessel dissociation, with evidence supporting that such activity is due to IP-10dp directly binding with and activating the CXCR3-B receptor. Experiments found that treatment of endothelial cells with the IP-10dp in vitro significantly inhibited VEGF-induced endothelial motility and tube formation, properties critical for angiogenesis. In vivo Matrigel assays also demonstrated that IP-10dp is able to inhibit vessel formation and induce vessel dissociation of nascent vessels. Inhibition of endothelial function by the IP-10dp is similar to that of the full ligand IP-10. CXCR3 neutralizing antibody is able to block the inhibitory effects of the IP-10dp and IP-10 in certain experiments, thus evidencing that both the full IP-10 ligand and IP-10dp operate through CXCR3. The peptides of the invention derived from fragments of IP-10 are thus able to inhibit endothelial cell motility, vessel formation and induce vessel dissociation via direct binding and activation of the CXCR3-B receptor.

Synthetic peptides according to the invention, such as IP-10dp and derivatives thereof, may be used in the treatment of cancers, such as breast cancer, and other tumorogenic diseases, used in the treatment of diseases characterized by unwanted vascular formation, or used in the treatment of chronic wounds (such as in a topical formulation for application to the site of the chronic wound.

In this regard, one embodiment of the invention includes compounds that comprise a synthetic peptide having a sequence that is at least 86% identical to SEQ ID NO: 1 and being less than 40 amino acids in length, and wherein said peptide binds with and activates CXCR3 receptor. Preferably, the peptide comprises IP-10dp, having the sequence SEQ ID NO: 1. Optionally, the compound may have one or more portions attached to said peptide sequence a portion selected from the group consisting of: a carrier portion to facilitate uptake by the intestine when the compound is administered orally to said mammal, a linking portion to link different portions of said compound together, and a targeting portion to target specific cells, receptors, or other biologic targets.

In this regard, other embodiments of the invention include methods of treating chronic wounds that comprise administering to a mammal in need thereof formulations that include compounds that comprise a synthetic peptide having at least a first domain, wherein: (a) the first domain is from 18-25 amino acids in length and comprises at least about 86% accuracy to the sequence SEQ ID NO: 1, and (b) exhibits the capability to activate CXCR3 in vivo in a mammal. Preferably, the peptide comprises the sequence SEQ ID NO: 1. Optionally, the peptide may have one or more domains in addition to the first domain and bound to the first domain, with the domains being joined together in any order. Such one or more additional domains may serve to, for example, link different domains together, function as a carrier to facilitate uptake by the intestine when the compound is administered orally to an animal (such as vitamin B12), target specific cells, receptors, or other biologic targets. Preferably, the peptide is less than 40 total amino acids. i.e., I guessed that the peptide should be approx. the size of a lytic peptide.

As each of the various compounds described above as comprising alternative and preferred embodiments of the invention have angiogenesis inhibiting activity, further aspects of the invention further include methods for inhibiting tumor growth or metastases in a mammal, comprising administering to the mammal an effective amount one or more of the of the compounds of the invention. Such methods for inhibiting according to the invention preferably are for inhibiting tumor growth or metastases in a mammal where said tumors are characterized by accelerated angiogenesis. Further, any of said methods may include administration of the compound to the mammal in any suitable fashion, including, for example, orally, intravenously, or parenterally.

As such, additional embodiments of the invention comprise pharmaceutical products that comprise a pharmaceutically effective amount of at least one compound according to the invention and a carrier. Additionally, the compounds of the present invention may be administered as described, or as pharmaceutically acceptable salts thereof.

The pharmaceutical products may be of any conventional form known in the art, including oral formulations, injectable formulations, transdermal formulations, transmucosal formulations, intravenous formulations, and the like.

For each of the various compounds described above as comprising alternative and preferred embodiments of the invention, other aspects of the invention further include polynucleotides that have an encoding region that encodes that compound, recombinant vectors which include those polynucleotides, and transformants that have inserted therein one or more of those recombinant vectors. Further, additional aspects of the invention include methods for producing one or more of the various compounds according to invention, which methods each include the step of culturing a transformant as described above so as to induce the transformant to produce at least one compound of the invention.

The various embodiments of the invention having thus been generally described, several illustrative embodiments will hereafter be discussed with particular reference to several attached drawings and in view of various experimental examples.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 6A is a grid of six black and white photographs, each photo depicting various epithelial cell cultures taken at 4× magnification.

FIG. 8 is a grid of seven color photographs (FIGS. 8A-8G) depicting tissue samples taken from laboratory C57BL/6J mice taken at various magnifications. FIG. 8D through FIG. 8G are color photographs of tissue samples, showing both 10× and 40× magnifications, taken from laboratory C57BL/6J mice. FIG. 8D is a representative sample at day 10 showing the VEGF-induced vessels formed in the Matrigel plug. FIG. 8E is a representative control sample at day 17 following saline administration. FIG. 8G is a representative test sample at day 17 following IP-10dp administration. FIG. 8F is a representative test sample at day 17 following IP-10 administration.

DETAILED DESCRIPTION OF THE PREFERRED EMBODIMENTS

Figure 1B:
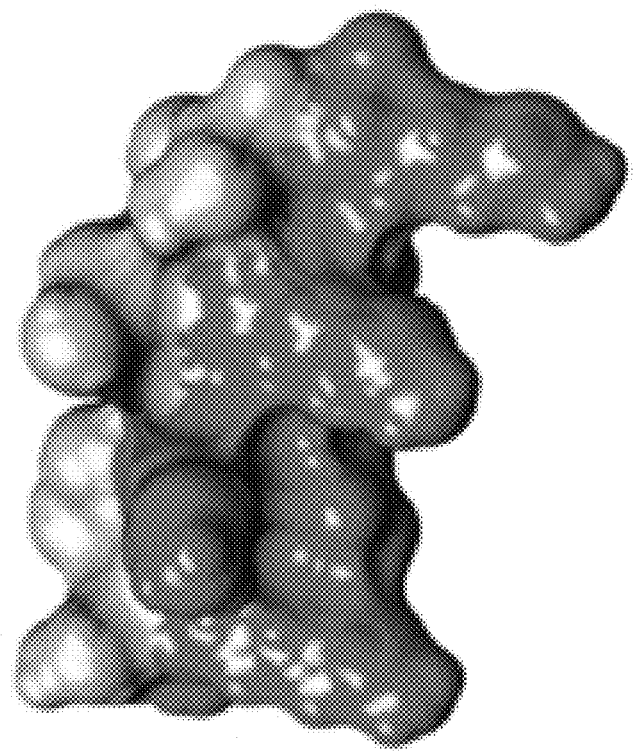
FIG. 1A and FIG. 1B are color drawings of three-dimensional molecular modelings of peptides IP-10 and IP10dp, respectively.

As used herein "effective amount" of a composition is an amount sufficient to retard or prevent angiogenesis, or to retard or prevent growth and/or metastases of a targeted tumor. Where appropriate in context, a "pharmaceutically effective amount" of a composition is an amount that is sufficient to retard or prevent unwanted angiogenesis, to retard or prevent growth and/or metastases of targeted tumor, or initiate remission of a targeted cancer when that amount is administered to a stricken animal as a pharmaceutical formulation.

Polynucleotides of the invention include any polynucleotide having a nucleotide sequence that encodes the peptides of the invention, although DNA is preferred. Exemplary DNA includes genomic DNA, genomic DNA libraries, cellular or tissue cDNA, cellular or tissue cDNA libraries, and synthetic DNA. The vectors used in the libraries are not subject to any particular limitation, and may be, for example, bacteriophages, plasmids, cosmids or phagemids. Also, amplification may be carried out directly by a reverse transcription polymerase chain reaction (abbreviated below as "RT-PCR") using total RNA or a mRNA fraction prepared from the above-mentioned cell or tissue.

Other hybridizable polynucleotides include, when calculations are done with a sequencing program such as FASTA or BLAST using the default parameters, DNA that is at least approximately 60%, at least approximately 65%, at least approximately 70%, at least approximately 75%, at least approximately 80%, at least approximately 85%, at least approximately 88%, at least approximately 90%, at least approximately 92%, at least approximately 95%, at least approximately 97%, at least approximately 98%, at least approximately 99%, at least approximately 99.3%, at least approximately 99.5%, at least approximately 99.7%, at least approximately 99.8%, or at least approximately 99.9% identical to polynucleotides encoding the subject amino acid sequence. The identity of an amino acid sequence or a nucleotide sequence can be determined using the above-described method.

Recombinant vectors of the invention include those that may be obtained by ligating (inserting) the polynucleotides of the invention to a suitable vector. More specifically, the recombinant vector may be obtained by cleaving purified polynucleotide (e.g., DNA) with a suitable restriction enzyme, then inserting the cleaved polynucleotide to a restriction enzyme site or multicloning site on a suitable vector, and ligating the polynucleotide to the vector. The vector for inserting the inventive polynucleotide is not subject to any particular limitation, provided it is capable of replication in the host. Vectors that may be used for this purpose include plasmids, bacteriophages, and animal viruses. Illustrative examples of suitable plasmids include plasmids from *E. coli* (e.g., pBR322, pBR325, pUC118 and pUC119), plasmids from *Bacillus subtilis* (e.g., pUB110 and pTP5), and plasmids from yeasts (e.g., YEp13, YEp24 and YCp50). An example of a suitable bacteriophage is the λ phage. Examples of suitable animal viruses include retroviruses, vaccinia viruses and insect viruses (e.g., baculoviruses).

Transformants of the invention include can those that may be created by introducing into a suitable host the recombinant vector, obtained as described above, which includes a polynucleotide of the invention (i.e., a polynucleotide encoding a peptide of the invention). The host is not subject to any particular limitation, provided it is capable of expressing the polynucleotide of the invention. Examples include bacteria of the genera *Escherichia, Bacillus, Pseudomonas* and *Rhizobium*, yeasts, animal cells and insect cells.

Introduction of the recombinant vector into the host and transformation thereby may be carried out by any of various commonly used methods. Examples of suitable methods for introducing the recombinant vector into the host cell include the calcium phosphate method (Virology, 52, 456-457 (1973)), lipofection (Proc. Natl. Acad. Sci. USA, 84, 7413 (1987)), and electroporation (EMBO J., 1, 841-845 (1982)). Examples of methods for transforming genus *Escherichia* bacteria include the methods described in Proc. Natl. Acad. Sci. USA, 69, 2110 (1972), and Gene, 17, 107 (1982). Methods for transforming genus *Bacillus* bacteria include the methods described in Molecular & General Genetics, 168, 111 (1979). Methods for transforming yeasts include the methods described in Proc. Natl. Acad. Sci. USA, 75, 1929 (1978). Methods for transforming animal cells include the methods described in Virology, 52, 456 (1973). Methods for transforming insect cells include the methods described in Bio/Technology, 6, 47-55 (1988). A transformant created by transformation with a recombinant vector containing the polynucleotide which codes for the peptide of the invention (i.e., the polynucleotides of the invention) may be obtained in this way.

One skilled in the art will understand that the subject peptides may be produced by culturing transformants of the invention under conditions that allow the polynucleotide encoding the peptide to be expressed, thereby inducing formation and accumulation of the inventive peptide, then isolating and purifying the peptide. It is well within the skill of one of ordinary skill in the art to select the appropriate conditions for causing expression for a given transformant, and to implement suitable mechanisms for isolating and purifying the peptide. The transformant of the invention may be cultivated by a conventional method used for culturing hosts. In such cultivation, the peptide of the invention may be formed by the transformant and accumulates within the transformant or the culture broth, requiring the selection of suitable isolation and purification processes.

Figure 1A:
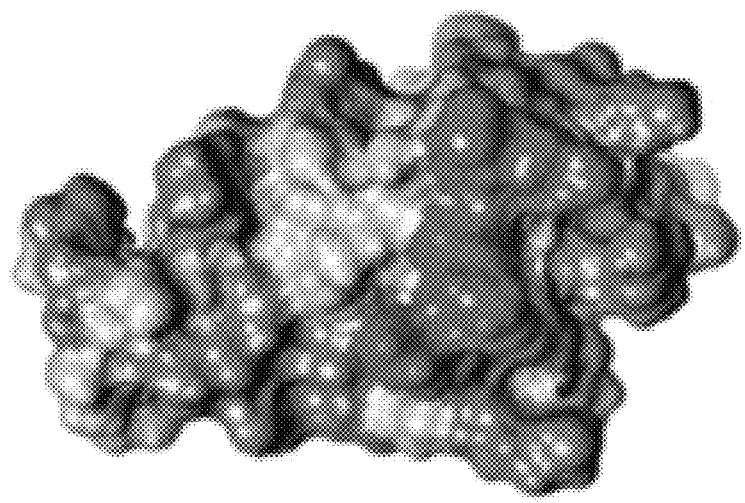

The chemokine derived peptides used in embodiments of the invention were designed by Applicant to be small yet have the ability to strongly target CXCR3. One preferred new peptide according to the invention, designated IP-10dp (SEQ ID NO: 1) was identified. Since cancer cells express high levels of CXCR3. FIG. 1A is a three-dimensional molecular modeling of full length IP-10 (SEQ ID NO: 2), while FIG. 1B is a similar molecular modeling of IP-10dp (SEQ ID NO: 1), both derived using the UCSF molecular modeling program Chiron.

Embodiments of the present invention are derived from epitopes of CXCL10 that are at least in part responsible for the inhibition of chemotaxis and calcium influx in endothelial cells. Prototypical of CXC chemokine topology, IP-10 secondary structure consist of an elongated N terminus that precedes the first cysteine, followed by a region of the structure which is between the second cysteine and the $3_{10}$ helix known as the N loop. This single-turn $3_{10}$ helix is succeeded by three β-strands and a C-terminal α-helix, with the β-strands of CXCL10 having been suggested as being the binding site responsible for receptor-mediated chemotaxis and calcium flux (see Swaminathan, 2003, supra). Embodiments of the present invention, however, embody the discovery that the C-terminal α-helix region of IP-10 yields the inhibitory function in endothelial cells that results in an anti-angiogenic biological function. Thus, synthetic peptides derived from this region but lacking the other regions of IP-10 should be, and are by the experiments herein confirmed to be, suitable as small peptide agonists that activate CXCR3-B and thus serve as therapeutics for in vivo treatment of mammals.

This particular region of IP-10 was targeted as being likely responsible for the activation of CXCR3 from an analysis of the IP-10 full length sequence for properties of similarity to other known angiostatic molecules. Known angiostatic molecules of particular relevance include lytic peptides, which are small basic proteins of about 23-39 amino acids that have the potential to form amphipathic-helices or partial-pleated sheets. These small oligo peptides are known in the art to interact with various membrane receptors. In this manner, the α-helical region of IP-10 was investigated as a possible agonist for CXCR3.

To evaluate the efficacy of these peptides in angiogenesis, a several experimental in vitro and in vivo experiments were conducted. In the various experiments described below, unless otherwise noted, the subject synthetic IP-10dp (SEQ ID. NO: 1) according to the present invention was synthesized by Polypeptide Laboratories (San Diego, Calif.) using standard fMoc chemistry procedures, pure by HPLC. Purification was conducted utilizing a Beckman HPLC fitted with a YMC C18, 4.6×250 mm column at 60° C., with a solvent system of A=0.1% TFA/H20, B=0.1% TFA/ACN at a flow rate of 1 ml/min (where TFA is trifluoroacetic acid and ACN is acetonitrile). Acceptable purity was confirmed using a LC/MS Finnigan MAT-LC/Q. For experimental use, all peptides were dissolved in sterile water.

In the various experiments described below, unless otherwise noted, the cell cultures of immortalized human microvascular endothelial cell line (Passages 21-25), denoted HMEC-1, was used. The HMEC-1 line was obtained from the Center for Disease Control (Atlanta, Ga.) and grown in 10% FBS-MDCB 131 media (obtained from Gibco, Gaithersburg, Md.) supplemented with 10 mM L-Glutamate (Gibco), 1 ng/ml EGF (obtained from BD Biosciences, Bedford, Mass.), 1 μg/ml hydrocortisone (obtained from Sigma, St. Louis, Mo.).

In the various experiments detailed below, unless otherwise noted, siRNA down regulation of CXCR3 was accomplished according to the following procedure. HMEC-1 cells were plated at $5.5 \times 10^5$ cells/60 mm dish and incubated overnight. The cells were 90-95% confluent. Cells were transfected with 4 μM siRNA (2 μM Sigma, 2 μM Santa Cruz) using Dharamacon #4 transfection reagent. The cells were incubated for 24 hours, and then placed in EGM-2MV media for 48 hours. The cells were then transfected again as indicated above. After 48 hours of incubation in EGM-2MV media the cells were then used for experimentation.

In the various experiments described below, unless otherwise noted, Biotin labeling was accomplished according to the following procedure. Sulfo-NHS-LC-Biotin (Thermo Scientific 21327) was prepared to result in a 10 mM solution of Biotin. IP-10, IP-10dp or anti-CXCR3 neutralizing antibody were dissolved in PBS according to result in a 20-fold molar excess of biotin reagent to give a 4-6 biotin groups per peptide molecule. The biotin reagent and IP-10 and/or IP-10dp was mixed and incubated on ice for 2 hours. Appropriate controls were used to determine the levels of biotin incorporation. HMEC-1 cells were washed in ice-cold PBS (pH 8) to remove amine-containing media and proteins. Cells were suspended and Sulfo-NHS-LC-Biotin label peptide was added. Mixture was incubated at 4° C. to reduce active internalization of the biotin reagent for 30 minutes. Cells were then washed three times in PBS+100 mM glycine to quench and remove excess biotin. Cells were then incubated with streptavidin conjugated with FITC and analyzed on a BD FACSCalbur flow cytometer.

In the various experiments described below, to the extent not otherwise noted, CXCR3 siRNA transfection was preformed according to the procedure as previously described by Koh et al. ("Methods in Enzymology," 2008, vol 443, p. 84), and summarized briefly as follows. HMEC-1 cells were plated in 6 well tissue culture plate at $4.0 \times 10^5$ cells/well in complete MCDB131 media and incubated overnight. The cells were ~75% confluent. The media was removed and replaced with serum free Opti-Mem and incubated for 30 minutes. Dharmafect #4 was added to Opti-Mem to a final concentration of 2.5% (final volume 200 ml) then incubated for 5 minutes at room temp. In parallel, CXCR3 siRNA was diluted in Opti-Mem to a final concentration of 200 mM (final volume 200 ml) then incubated for 5 minutes at room temp. CXCR3 siRNA was a pool of equal concentration from Sigma and Santa Cruz. The Dharmafect solution was added to the CXCR3 siRNA pool and incubated for 20 minutes at room temp. The Dharmafect/siRNA solution was diluted with 1.6 mls of complete MCDB131 media then added to a well and incubate for 6 hours at 37° C. with 5% $CO_2$. The media was removed and replaced with complete MCDB131 media. Cells were incubated for 48 hrs at 37° C. with 5% $CO_2$. After 48 hrs the cells were transfected a second time as indicated above. The cells were incubated for 36 hours in complete MCDB131 media at 37° C. with 5% $CO_2$ then detached for use. Staining for CXCR3 was using to detect expression.

In the various experiments described below, unless otherwise noted, real-time imaging of cell cultures was performed utilizing an Olympus DSU (Disk Scanning Units) Confocal microscope (Olympus America Inc., PA). The subject cells were maintained in 5% $CO_2$ at 37° C. in an incubation chamber (Pathology Devices, Inc., MD). Images were processed utilizing MetaMorph Imaging Software (Molecular Devices, CA).

For all experiments, unless otherwise noted, statistics were performed with Microsoft Excel. All quantitative assays were performed at least 6 times each in triplicate experiment. All animal assays were performed on a minimum of 6 mice. Results are expressed as mean±SEM per specimen or experiment because all individual assays measurements were performed in replicate. Statistical differences between groups were determined by 2-tailed Student's t-test. Paired analyses were performed between all groups. Statistical significance is set at P<0.05 for all reported results.

Several preferred embodiments of the various inventions of the present invention will now be illustrated by the following discussion of several laboratory experiments and associated laboratory data.

EXPERIMENT 1

Figure 2:
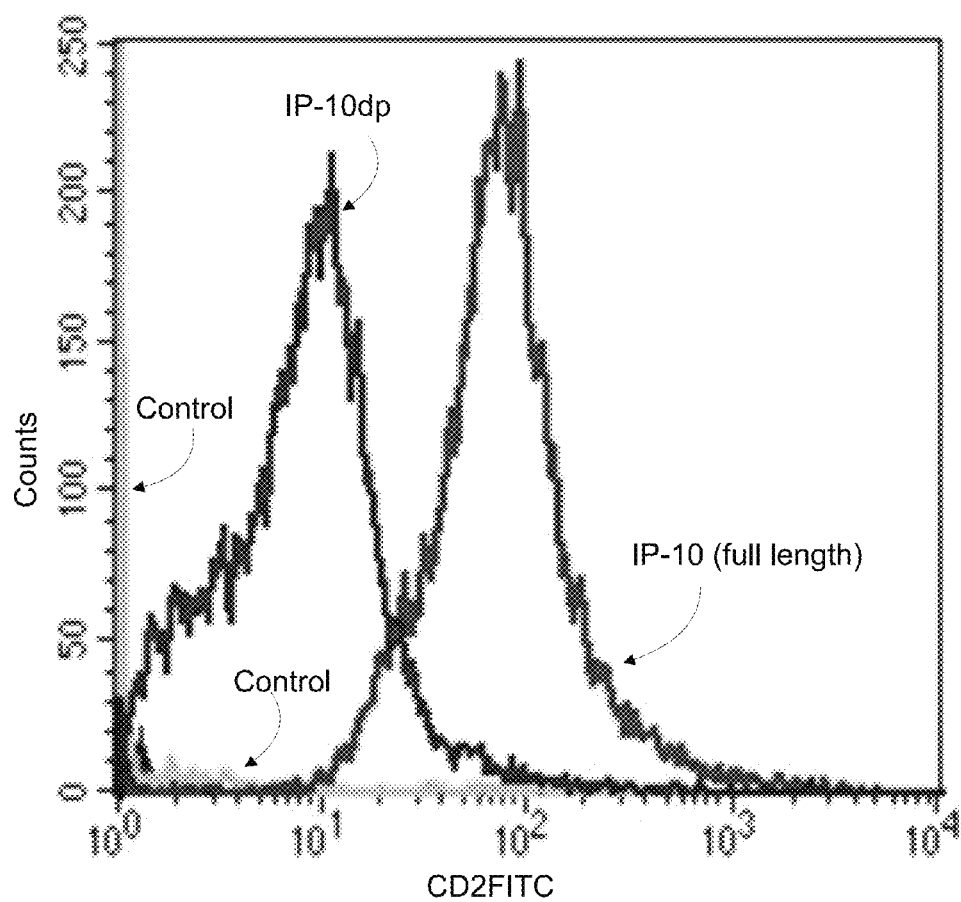
FIG. 2 is a graph reporting experimental results comparing the binding of IP-10 and IP-10dp to epithelial cells.

To determine whether IP-10dp binds to CXCR3 on human dermal microvascular endothelial cells, we analyzed the ability of Sulfo-LC-Biotin tagged IP-10 and IP-10dp to bind to H MEC-1 cells using flow cytometery. As noted above, HMEC-1 cells express CXCR3, and IP-10 is known to binds to CXCR3 in a functional angiostatic capacity. In this experiment, HMEC-1 cells were plated, detached, and fixed in 2% formaldehyde-Hank's balanced salt solution. IP-10 and IP-10dp was labeled using LC-biotin tags. The cells were then incubated with FITC conjugated with streptavidin, and then analyzed on a BD FACSCalbur flow cytometer. FIG. 2 is a graph reporting results from this experiment by comparing the binding of IP-10 and IP-10dp to the HMEC-1 cells.

As shown in the graph of FIG. 2, the data from this experiment showed that, relative to control, IP-10dp has a slightly lower fluorescence intensity of binding to CXCR3 on the HMEC-1 cells than that for full length LP-10. This lower fluorescent signal observed for the IP-10dp-bound HMEC-1 cells, however, does not indicate IP-10dp has a lower affinity for CXCR3 than full length IP-10. The LC-Biotin tagging used in the experiment was at a molar concentration to specifically target the leucine-leucine motif found in the peptide α-helix of IP-10. While IP-10dp only contains 2 leucines, IP-10 has 10 leucines within its amino acid sequence allowing for up to a 5-fold difference in bound biotin. Thus, a significant difference in fluorescent intensity between bound IP-10dp and IP-10 protein was expected. While the data from this experiment does not determine the affinity of IP-10dp for CXCR3, it does show that IP-10dp in fact binds to human endothelial cells.

EXPERIMENT 2

To determine whether IP-10dp inhibits endothelial cell motility, a conventional "scratch assay" was performed. ELR-negative chemokines, such as IP-10, inhibit fibroblast and endothelial cell motility. IP-10 has been shown in prior literature to inhibit HMEC-1 cells' motility in the presence of angiogenic growth factors VEGF165 and bFGF. Thus, a scratch assay comparison was conducted to examine whether, and to what extent, IP-10dp could mimic the inhibitory effects of the full length IP-10. HMEC-1 cells were plated at 2.5×10$^5$ cells/well in 12 well culture plates and grown to 80 to 85% confluence and quiesced in 0.5% dialyzed fetal bovine serum for 24 hours at 37° C. in 5% $CO_2$. The cells were washed one time with PBS and then incubated in 0.5% dialyzed MDCB 131 media for 24 hours at 37° C. in 5% $CO_2$. The cultures were scraped with a rubber policeman making a 1 mm wide denuded area. The cells were then incubated in 0.5% dialyzed either alone (i.e., a control labeled as "NT," for no treatment, in FIG. 3) or stimulated with IP-10 (200 ng/ml), IP-10dp (10 µM), VEGF (100 ng/ml), IP-10 plus VEGF, or IP-10dp plus VEGF for 24 hours at 37° C. in 5% $CO_2$. Images were taken at time zero and 24 hours, and the relative distance traveled by the cells into the a cellular area was determined using Meta-Morph. The HMEC-1 culture images were analyzed for the ability of the cells to migrate into a denuded area over a 24 hour period in the presence or absence of VEGF165.

Figure 3:
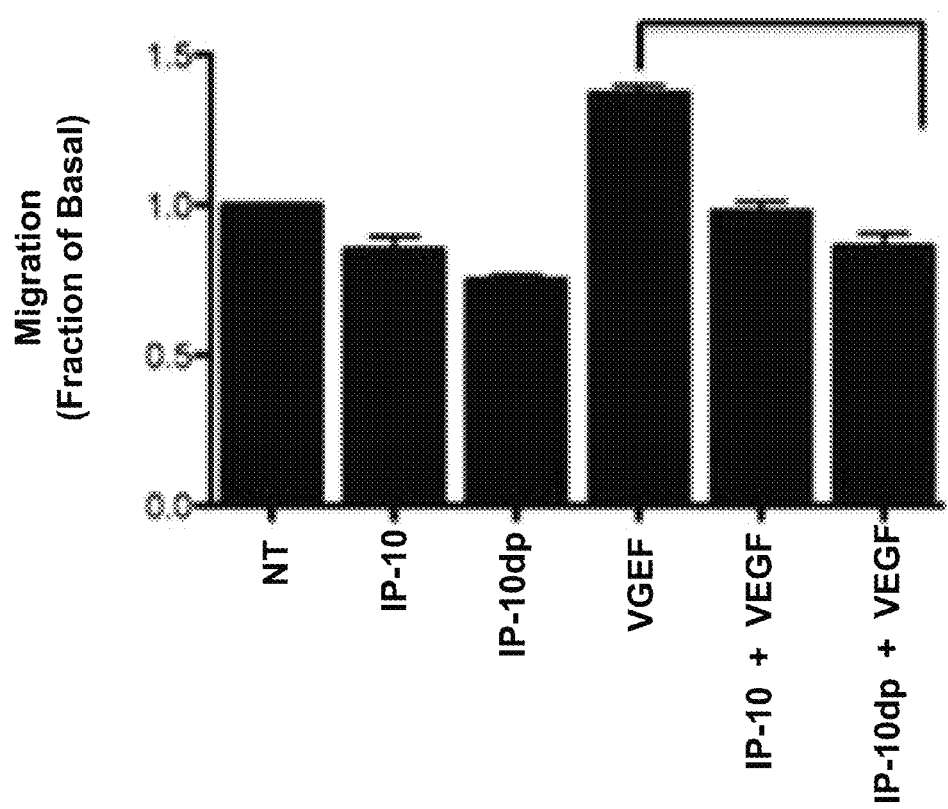
FIG. 3 is a graph reporting experimental results for a scratch assay of epithelial cells.

FIG. 3 is a graph reporting the experimental results for these scratch assays, with the reported results being N=6 (average±SEM) *P<0.05. As expected, IP-10dp inhibited motility of the HMEC-1 cells, both with and without stimulation with VEGF (i.e., VEGF-induced induced motility). Further, IP-10dp was found to have a greater inhibition of endothelial cell migration than observed with IP-10. Although this inhibition was only 10% greater than what was observed for IP-10, it was statistically significant. These data show that IP-10dp is functional and has a greater inhibitory effect than recombinant IP-10.

EXPERIMENT 3

As noted above, ELR-negative chemokines have been shown to limit vascularity by regulating the ability of endothelial cells to form vessels in vitro. To determine whether the IP-10 peptide is able to inhibit tube formation, HMEC-1 cells were grown on growth factor reduced ("GFR") Matrigel in the presence of VEGF165, IP-10 and/or IP-10dp and the cultures inspected and compared to asses the relative degree of tube formation according to the following procedure. GFR Matrigel 10 µl/well (µ-angiogenesis slide, Ibidi), was incubated for 15 minutes at 37° C. HMEC-1 cells (10,000 cells/well) were re-suspended in 1.0% FBS MDCB131 media containing VEGF (75 ng/ml), IP-10 (300 ng/ml) and IP-10dp (10 µM) and or anti-CXCR3 neutralizing antibody. Treated cells (1×10$^4$ cells/well) were added to 24-well culture plates coated with growth factor reduced Matrigel and incubated for 24 hours at 37° C. to allow tube formation. The media was then removed and replaced with 1.0% FBS MCDB131 media containing combinations of VEGF (75 ng/ml), IP-10 (300 ng/ml) and IP-10dp (10 µM) as indicated in FIG. 4, and then further incubated for 24 hours at 37° C. in 5% CO2.

Figure 4A:
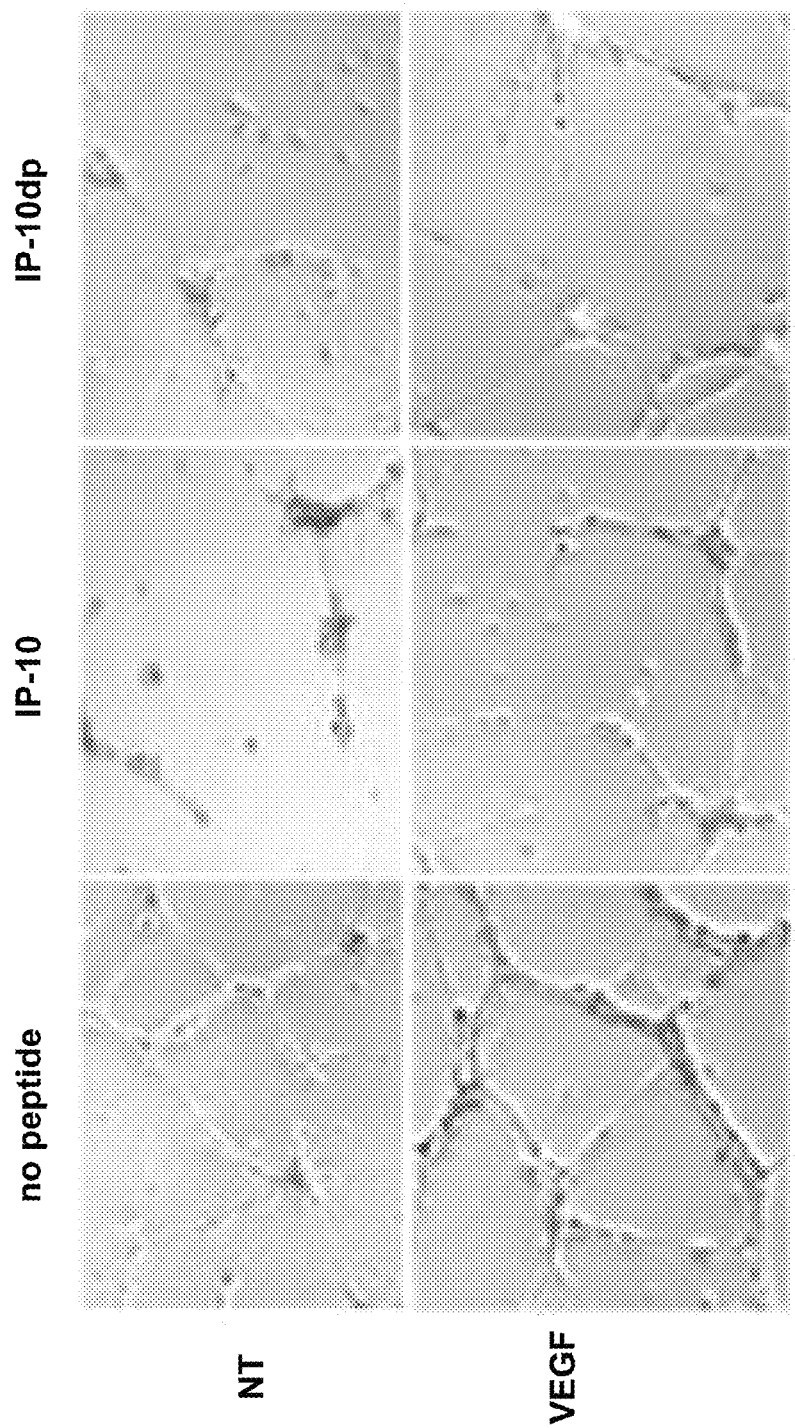
FIG. 4A is a grid of six black and white photographs, each photo depicting various epithelial cell cultures taken at 4× magnification.

The cells cultures were then imaged for tube formation using an Olympus IX70 microscope equipped with a Hammastu camera using MetaView™ software (Universal Imaging Corporation, Downington, Pa.). FIG. 4A is a grid of six labeled black and white photographs taken at this 24 hour point with 4× magnification showing the following representative cell cultures from upper left to lower right: a control culture having no treatment, a culture having treatment only with IP-10, a culture having treatment only with IP-10dp, a culture having treatment only with VEGF, a culture having treatment with combined VEGF and IP-10, and a culture having treatment with combined VEGF and IP-10dp.

Figure 4B:
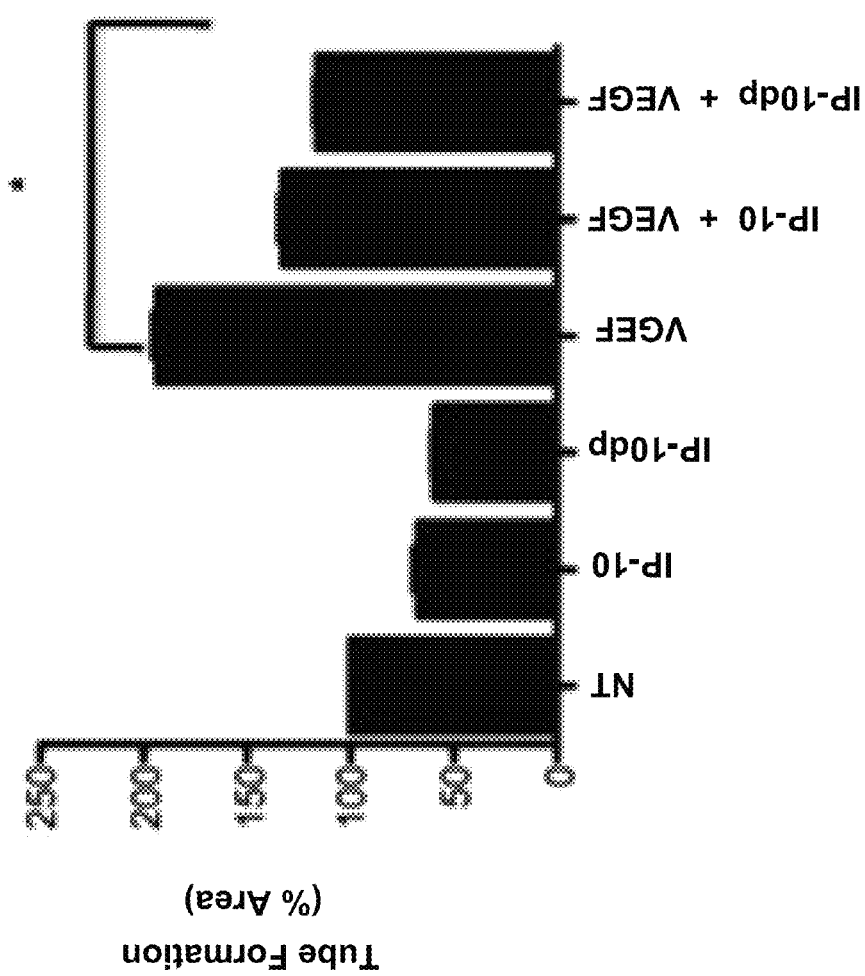
FIG. 4B is a graph comparing experimental results measuring new tube formation within the cell cultures including those depicted in FIG. 4A.

Analysis of tube formation was preformed using Meta-Morph (obtained from Universal Imaging Corporation, Downington, Pa.), and the results reported in the graph of FIG. 4 are shown as a percent of the no-treatment control. The data reported therein are of N=6 and normalized to no treatment (average±SEM), with *P<0.05. As shown by the graph, IP-10 peptide is able to inhibit tube formation. In particular, after incubation for 24 hours, the HMEC-1 cells cultures were able to form tubes in the presence or absence of VEGF165 (compare the photographic images in FIG. 4A). When HMEC-1 cells were incubated with IP-10dp there was a significant reduction in tubes formed compared to control (see FIG. 4A). A significant reduction was also seen in the cells cultured in the presence of both IP-10dp and VEGF165 (see FIG. 4A) Quantification of the tubes in each culture type relative to control established that IP-10dp was able to inhibit tube formation slightly better than that observed for full length IP-10 in the presence and absence of VEGF (see FIG. 4B).

EXPERIMENT 4

Although the data from the experiments above established that IP-10dp inhibits cells migration and thus inhibits tube formation, the present experiment was conducted to verify whether IP-10dp was able to induce dissociation of newly formed tubes. For this tube dissociation assay, HMEC-1 cells were first re-suspended in 1% FBS MCDB131 media containing VEGF (75 ng/ml) and incubated on GFR-Matrigel for 24 hrs at 37° C. to allow tube formation (the average result reflected labeled "24 VEGF . . . " in FIG. 5B). The media was removed and replaced with combinations of VEGF (75 ng/ml), IP-10 (300 ng/ml), or IP-10dp (10 μM) then incubated for another 24 hours. After 48 hours, tubes were still present in the controls treated only with VEGF (labeled 48 hr VEGF in FIG. 5B).

Figure 5A:
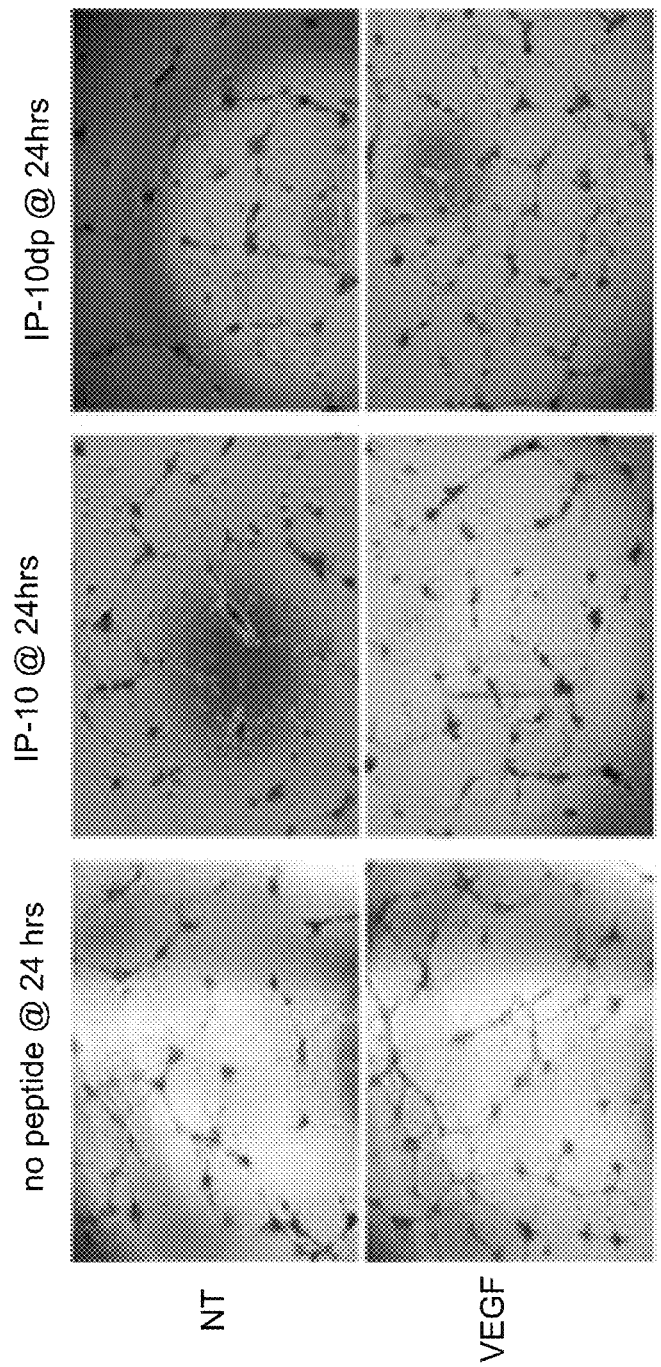
FIG. 5A is a grid of six black and white photographs, each photo depicting various epithelial cell cultures taken at 4× magnification.

The cells cultures were imaged to assess tube formation using similar procedures to that described above for Experiment 3. The six black and white photographs depicted in FIG. 5A were taken at the 48 hr point with 4× magnification showing the following representative cell cultures (from upper left to lower right): a control culture having no treatment from 24-48 hrs, a culture having treatment only with IP-10 from 24-48 hrs, a culture having treatment only with IP-10dp from 24-48 hrs, a culture having treatment only with VEGF from 24-48 hrs, a culture having treatment with combined VEGF and IP-10 from 24-48 hrs, and a culture having treatment with combined VEGF and IP-10dp from 24-48 hrs.

Figure 5B:
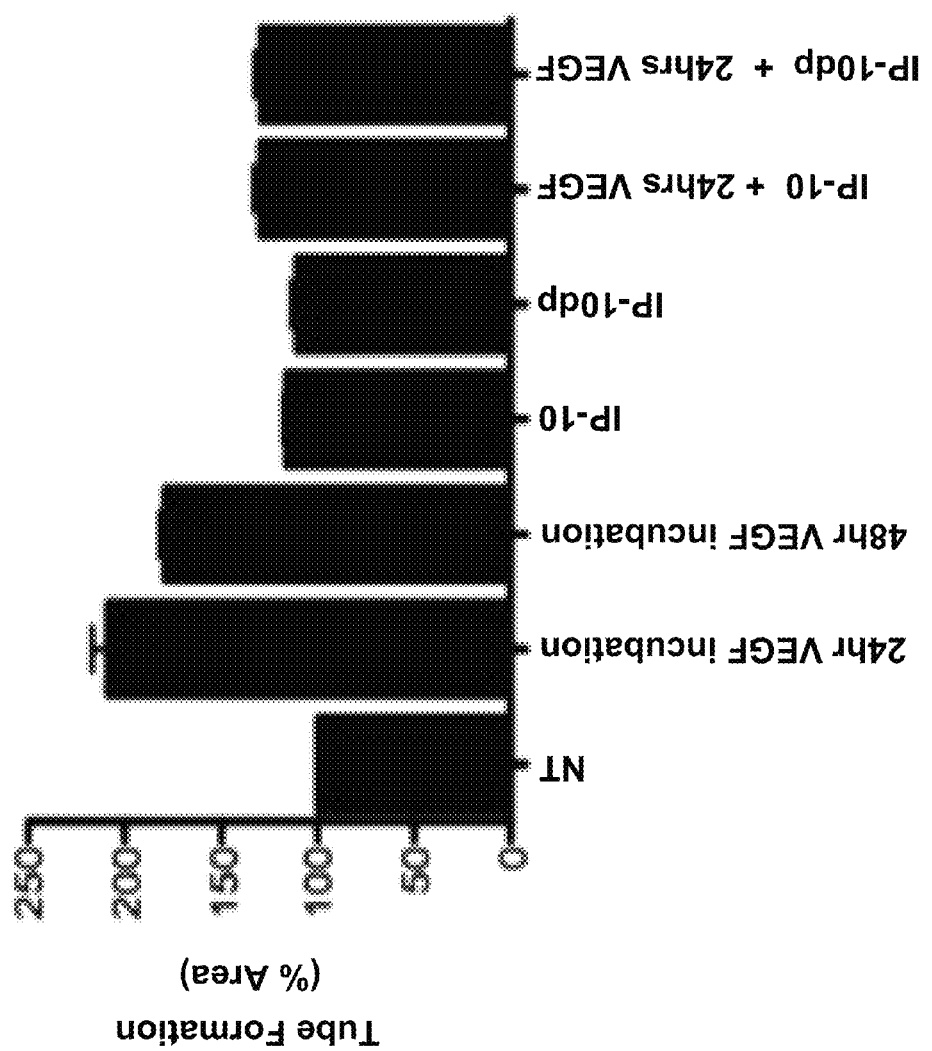
FIG. 5B is a graph comparing experimental results measuring existing tube dissociation within the cell cultures including those depicted in FIG. 5A.

Again, quantification of the endothelial tube area for the various cell cultures was determined using MetaMorph, and the data reported in the graph are of at least N=6 and normalized to no treatment (average±SEM), with $*P<0.05$. As shown in the graph of FIG. 5B, both IP-10 and IP-10dp induce dissociation of newly formed tubes, both in the presence of VEGF and in the absence of VEGF. A significant decrease in endothelial cords was observed following treatment with IP-10dp.

Collectively, the data from this experiment supports a conclusion that IP-10dp is able to cause tube dissociation cause by CXCR3 signaling. Thus, it would be likely be effective in reversing the initial stages of angiogenesis as well as preventing unwanted angiogenesis.

EXPERIMENT 5

As noted above, ELR-negative chemokine IP-10 inhibitory affect on endothelial cells has been shown to be meditated via CXCR3 signaling. To determine if the IP-10dp peptide is acting through the same signaling pathways as IP-10, an experiment was conducted using a CXCR3-neutralizing antibody (also referred to herein as CXCR3 Ab) to assess that antibody's impact upon IP-10dp's ability to block tube formation. HMEC-1 cells were grown, detached and re-suspended in serum-free media and all were pretreated with CXCR3 Ab (0.5 μg/ml) 30 minutes prior to the addition of VEGF (75 ng/ml), IP-10 (300 ng/ml), IP-10dp (10 μM) and/or Immunoglobulin G (or "IgG," as control). The thus-treated cells ($1\times10^4$ cells/well) were added to 24-well culture plates coated with growth factor reduced Matrigel and incubated for 24 hours, and endothelial tubes were allowed to form as described above. Images were obtained as above. As seen in the black and white photographs depicted in FIG. 6A, the CXCR3-neutralizing antibody blocked IP-10dp inhibitory affect. Taken at 4× magnification, those photographs are of the following representative cell cultures (from upper left to lower right of FIG. 6A): a control culture having treatment with IgG as control (labeled "NT" in the figure to represent no treatment besides CXCR3 Ab pre-treatment), a culture having treatment only with IP-10, a culture having treatment only with IP-10dp, a culture having treatment only with VEGF, a culture having treatment with combined VEGF and IP-10, and a culture having treatment with combined VEGF and IP-10dp.

Figure 6B:
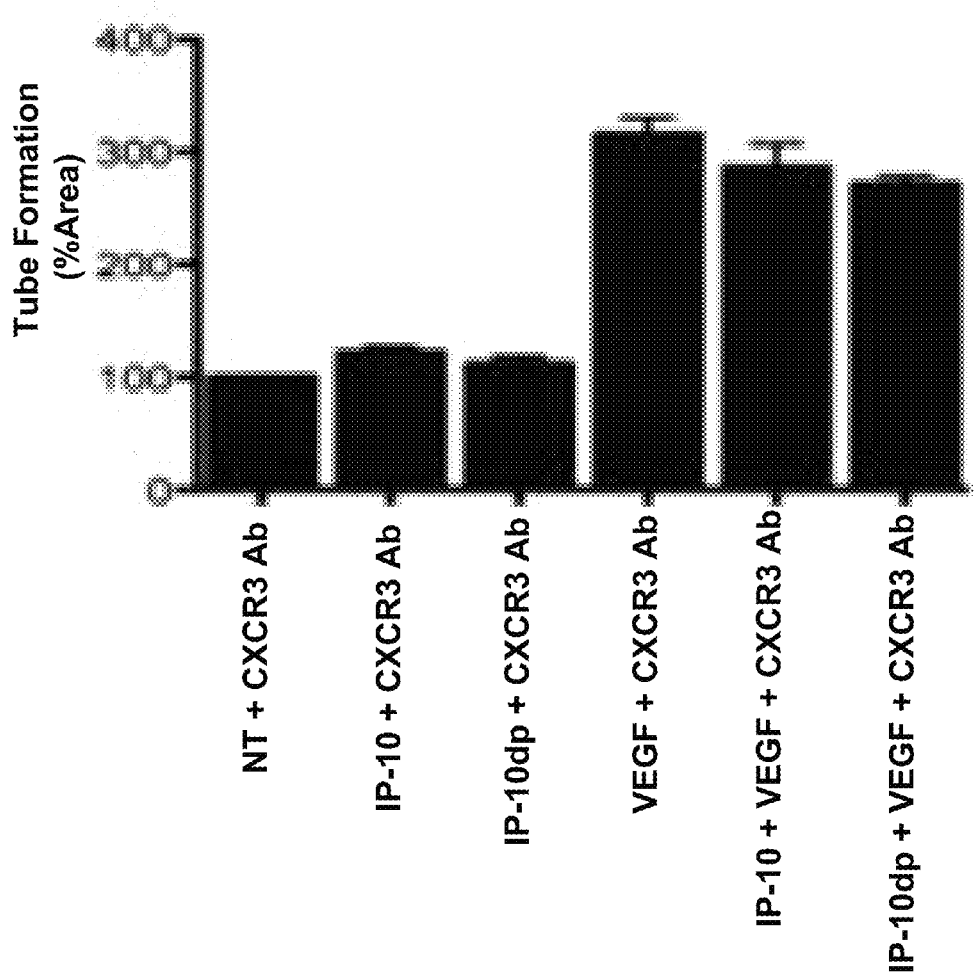
FIG. 6B is a graph comparing experimental results measuring the impact of neutralizing antibody CXCR3 on new tube formation within the cell cultures including those depicted in FIG. 6A.
Figure 6C:
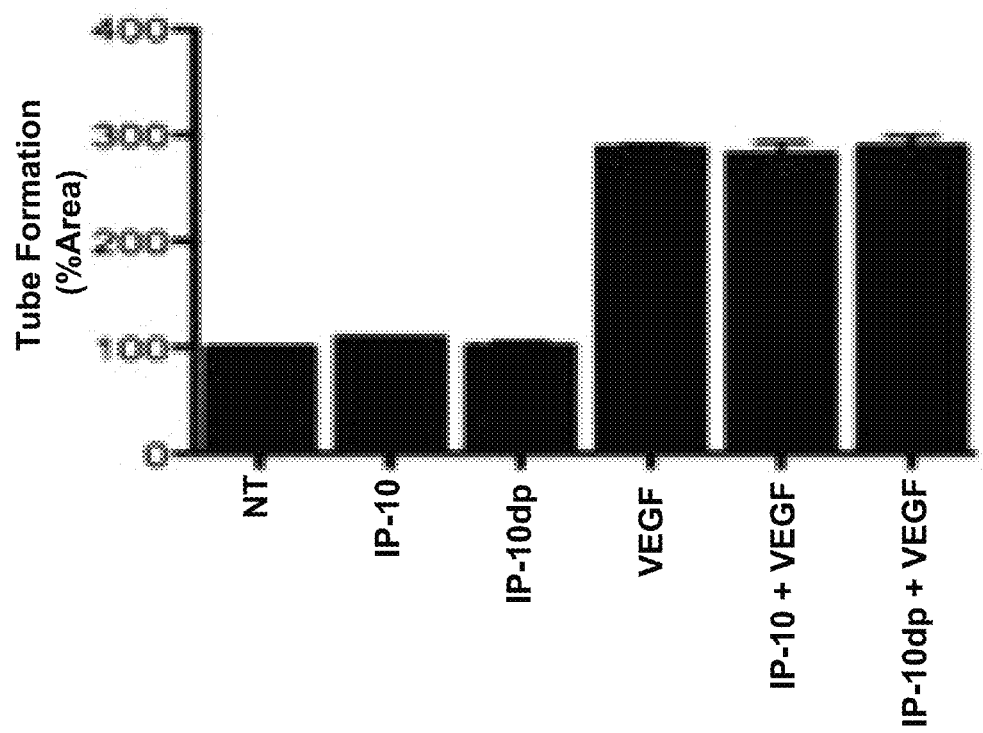
FIG. 6C is a graph comparing experimental results measuring the impact of CXCR3 siRNA down regulation of CXCR3 on new tube formation within the cell cultures including those depicted in FIG. 6A.

Quantification of the endothelial tubes formed was performed as above, using MetaMorph, with the data being shown in the graphs of FIG. 6B are of N=6 and normalized to no treatment (average±SEM), and with $*P<0.05$. As shown in FIG. 6C, as expected, incubation with VEGF showed a significant enhancement in the number of tubes formed. Further, tube formation inhibition mediated by IP-10dp and IP-10, which was detected in Experiment 3 above, was significantly blocked by this pre-treatment with CXCR3 Ab. IP-10dp (like IP-10) was unable to override the angiogenic signals from VEGF, and tube formation occurred in the presence of VEGF when CXCR3 receptor was neutralized. These data strongly suggest that the IP-10dp fragment inhibitory affect on endothelial cells is CXCR3 receptor mediated.

EXPERIMENT 6

To further verify that the inhibitory effect of IP-10dp is mediated through CXCR3, HMEC-1 cells were treated with CXCR3 siRNA, Knockdown of CXCR3 in these cells was verified by immunostaining for CXCR3. The CXCR3 siRNA-mediated down regulated cells showed no staining for CXCR3, where as cells transfected with control siRNA showed significant CXCR3 staining. These siRNA-treated cells were then incubated on GFR Matrigel in the presence of concentrations of VEGF, IP-10, and/or IP-10dp in the manner as described above in Experiment 3. Unlike the untreated HMEC-1 cells in Experiment 3, these siRNA-treated cells did not show a significant difference in the formation of tubes in the presence of IP-10 or IP-10dp. As shown in the graph of FIG. 6C, the tube density of the siRNA-mediated knockdown cells was similar to non-specific siRNA treated cells and untreated HMEC-1 cells incubated in the absence of IP-10dp. The results of this experiment thus further supports that the inhibitory affect of the IP-10dp peptide on endothelial cells is CXCR3 receptor mediated.

EXPERIMENT 7

Figure 6D:
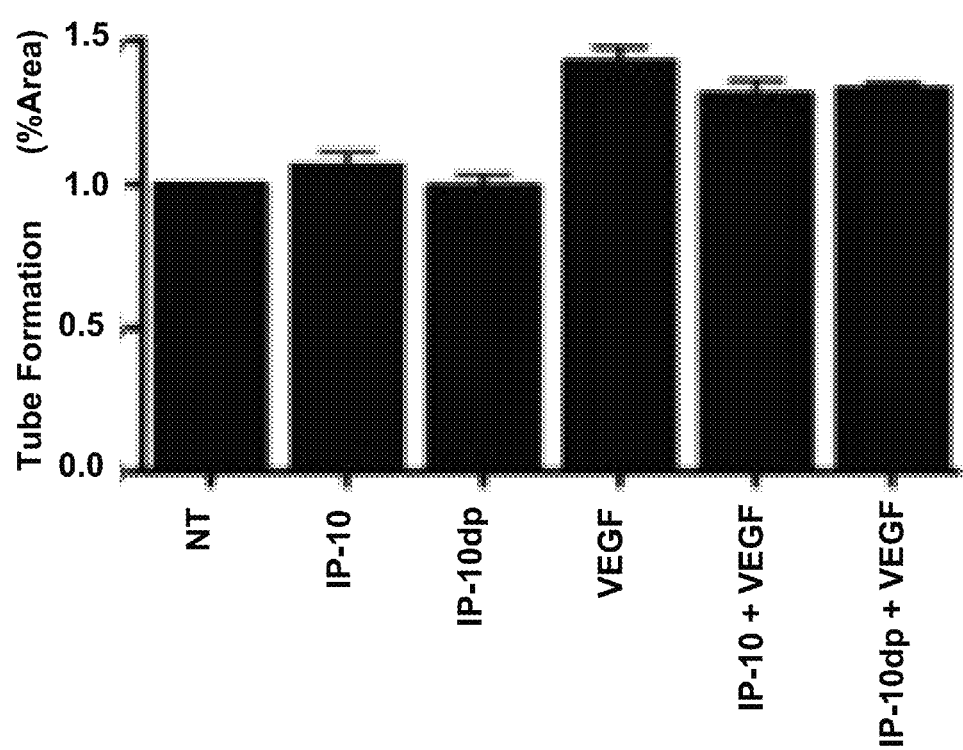
FIG. 6D is a graph comparing experimental results for a scratch assay of epithelial cells after CXCR3 siRNA down regulation of CXCR3.

To further verify that the inhibitory effects of IP-10 and IP-10dp are both through the CXCR3 receptor, additional HMEC-1 cells transfected with CXCR3 siRNA were utilized in a scratch assay according to the procedure described above in Experiment 2. For these transfected cells, as shown in FIG. 6D neither IP-10 nor IP-10dp inhibited endothelial migration of cells into the denuded space (i.e., were unable to inhibit VEGF-induced motility). Together, Experiments 5-7 show the inhibitory effects of IP-10dp on VEGF-induced tube formation and cell migration is due to activation of CXCR3.

EXPERIMENT 8

Figure 7A:
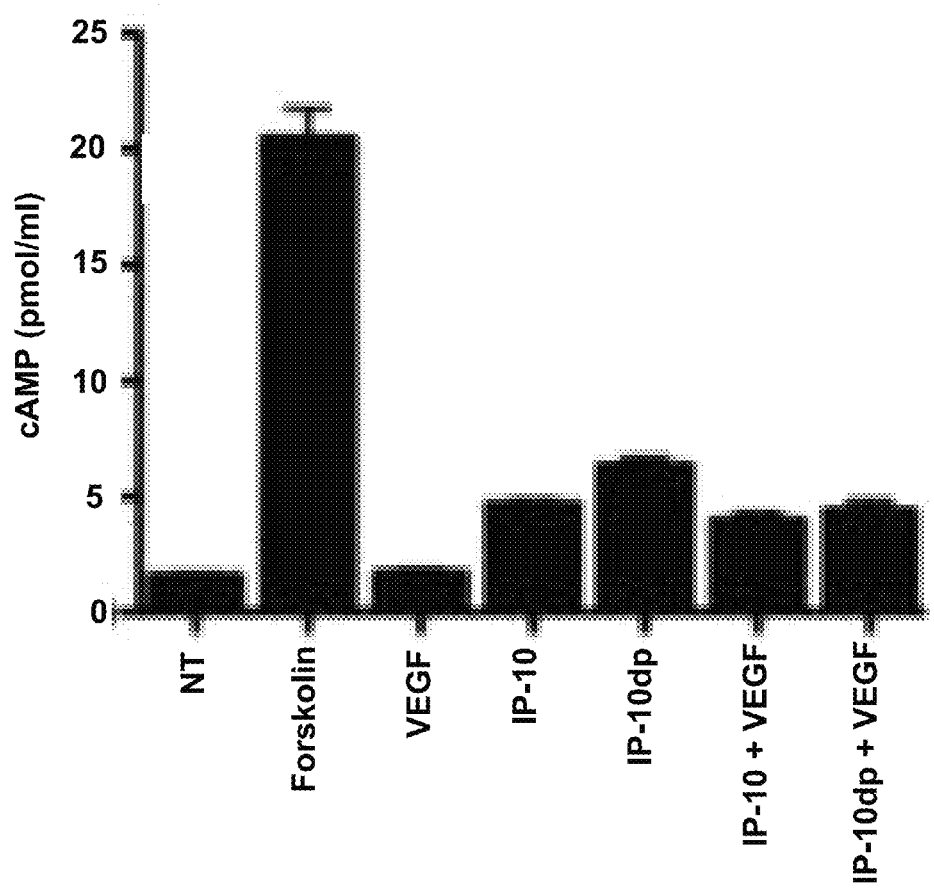
FIGS. 7A and 7B are graphs comparing experimental results for assays measuring stimulation in epithelial cells of cyclic adenosine monophosphate ("cAMP") and protein kinase A ("PKA"), respectively.

As noted above, even though IP-10 has been shown to induce cAMP activation of PKA in endothelial cells and fibroblasts and be required for inhibition tube formation and motility, cAMP is not increased when keratinocytes are exposed to IP-10. Thus, an experiment was conducted to determine if stimulation of endothelial cells with IP-10dp would induce an increase in cAMP. HMEC-1 cells were plated in 10 mm culture dishes and grown to confluency in complete growth media. The cells were then incubated in serum-reduced media (0.5% dialyzed FBS for HMEC-1 cells) for 24 hours at 37° C. The cells were then washed once with PBS and incubated in serum-free media. The cells were then stimulated with forskolin (25 mM), VEGF (100 ng/ml), IP-10 (200 ng/ml), IP-10dp (10 μM) alone or in various combinations. The media was removed and ice cold 80% ethanol was added and the cells incubated on ice for 15 minutes. The extracts were evaluated and quantified for total cAMP production by using a cAMP enzyme immunoassay kit provided by Sigma-Aldrich Corp., of St. Louis, Mo., according to the manufacturer's protocol. As shown in the graph of FIG. 7A, The HMEC-1 cells treated with IP-10dp showed a 2-3-fold increase in cAMP production compared to control and VEGF treated cells. When the cells were stimulated with a combination of VEGF and IP-10dp, there was still a significant increase in cAMP production compared to VEGF alone. These results indicate that incubation of endothelial cells with IP-10dp induces the formation of cAMP, which in turn could lead to the activation of PKA in the CXCR3 signaling pathway.

EXPERIMENT 9

To further investigate the cAMP activation of PKA, a PKA assay experiment was conducted. As above, HMEC-1 cells were grown in complete growth media then further incubated in 0.5% dialyzed FBS MCDB 131 media for 24 hours. The cells were then stimulated with forskolin (25 mM), and/or combinations of VEGF (100 ng/ml), IP-10 (200 ng/ml), and/or IP-10dp (10 μM) for 15, 30 and 60 minutes. The cells were lysed with an ice-cold hypotonic solution (50 mM Tris pH 7.4, 1 mM EDTA, 10 mg/ml aprotinin and 1 mM PMSF). The cells were incubated on ice for 30 minutes then centrifuged to remove the cell membranes. PKA activity was measured using a commercially available cAMP dependent protein kinase kit (Non-Radioactive Detection kit, from Promega Corp., of Madison, Wis.) according to the manufacturer's protocol. Absorbance was read at 570 nm with the solubilization buffer serving as a blank. The graph of FIG. 7B shows the amount of the synthetic substrate phosphorylated by PKA.

Figure 7B:
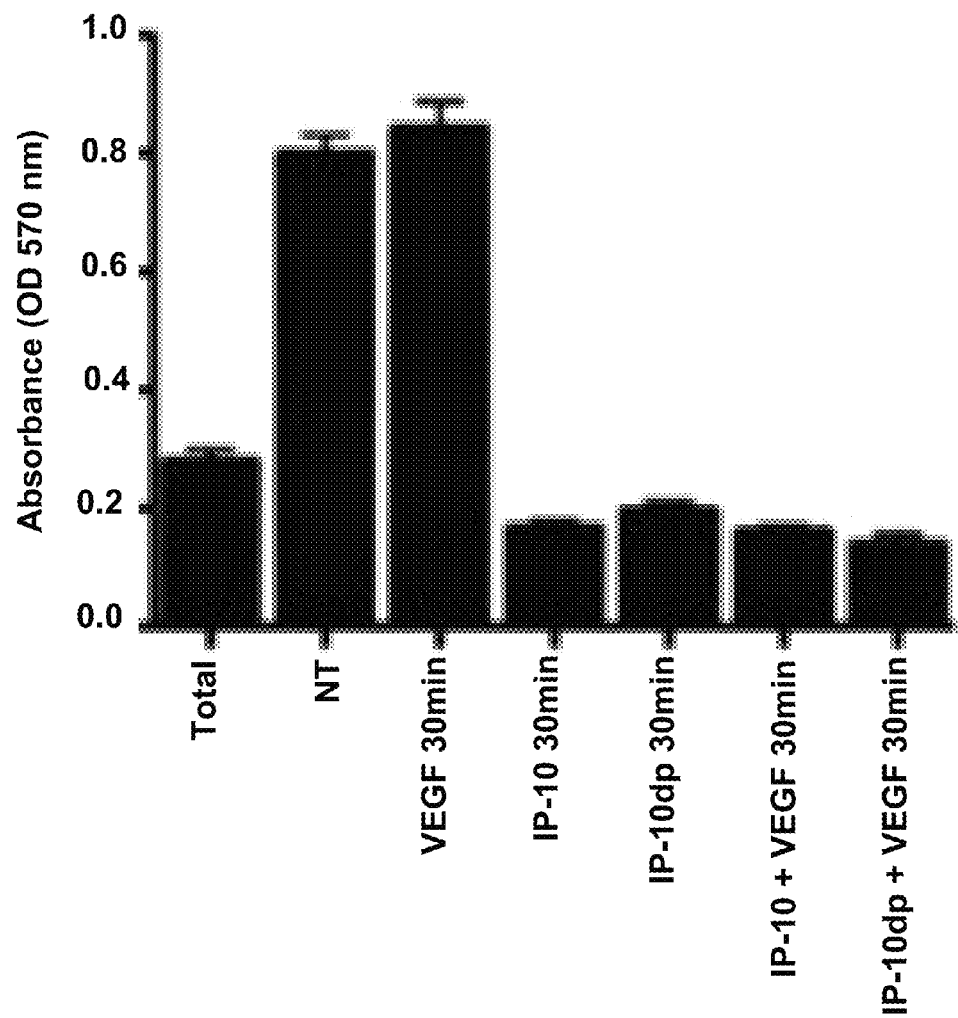

As shown in the graph of FIG. 7B, incubation of HMEC-1 cells with IP-10dp showed a significant increase in PKA activity in comparison to VEGF and untreated cells, with IP-10dp showing a 2-3 fold increase in c. These results suggest that IP-10dp induces the activation of PKA.

EXPERIMENT 10

Prior research has also shown that in endothelial cells, the CXCR3-activation of PKA inhibits motility secondary to inhibitory phosphorylation of m-calpain (also known as "CAPN1"). VEGF induces calpain activity in endothelial cells, and μ-calpain (also known as "CAPN2") is activated, at least in part, by ERK phosphorylation on serine 50 and in other cells μ-calpain is activated secondary to a calcium flux. In this experiment, the IP-10dp affect on m-calpain is studied by using the membrane permeable synthetic calpain substrate Boc-LM-CMAC. Since the pre-fluorescent substrate Boc-LM-CMAC can be cleaved by both m- and μ-calpain, this experiment used BAPTA/AM, a membrane permeable calcium chelator, to distinguish between m- and μ-calpain activation in cells as this blocks activation of μ-calpain but not m-calpain.

In order to establish whether the IP-10dp inhibition of motility involves this above-described blockade of calpain activation, 8 well chamber slides were coated with 0.1% gelatin for 24 hours at 4° C. The gelatin was removed and HMEC-1 cells were plated at 12,000 cells/well then incubated in 10% FBS-EBM-EC media for 24 hrs. The media was removed and the cells were further incubated for 12 hrs with 0.5% dialyzed FBS-EBM media. All cell cultures were then incubated with either BAPTA AM (5 mM), or Calpain inhibitor I (CI-1, 10 mM) at 37° C. for 30 minutes. BOC-LM-CMAC (Boc) (25 μM, Molecular Probes) was added and incubated at 37° C. for 30 minutes, then VEGF (75 ng/ml), IP-10 (200 ng/ml), and IP-10dp (10 μM) were added in different combinations to various cultures and incubated for 30 minutes at 37° C. For some cultures, the addition of cAMP analogs 8-Br-cAMP (50 μM), an activator of PKA, and Rp-8-Br-cAMP (250 μM), an inhibitor of PKA, were added 20 minutes prior to the addition of Boc. The cells were then placed under a coverslip and analyzed for cleavage of Boc by fluorescence microscopy, and digital images were captured using a Spot RTke digital camera and Spot software. Calpain activity was quantified by MetaMorph analysis, with the data shown in FIG. 7D being representative of at least N=9 and normalized to no treatment (average±SEM), with *P<0.05.

Figure 7C:
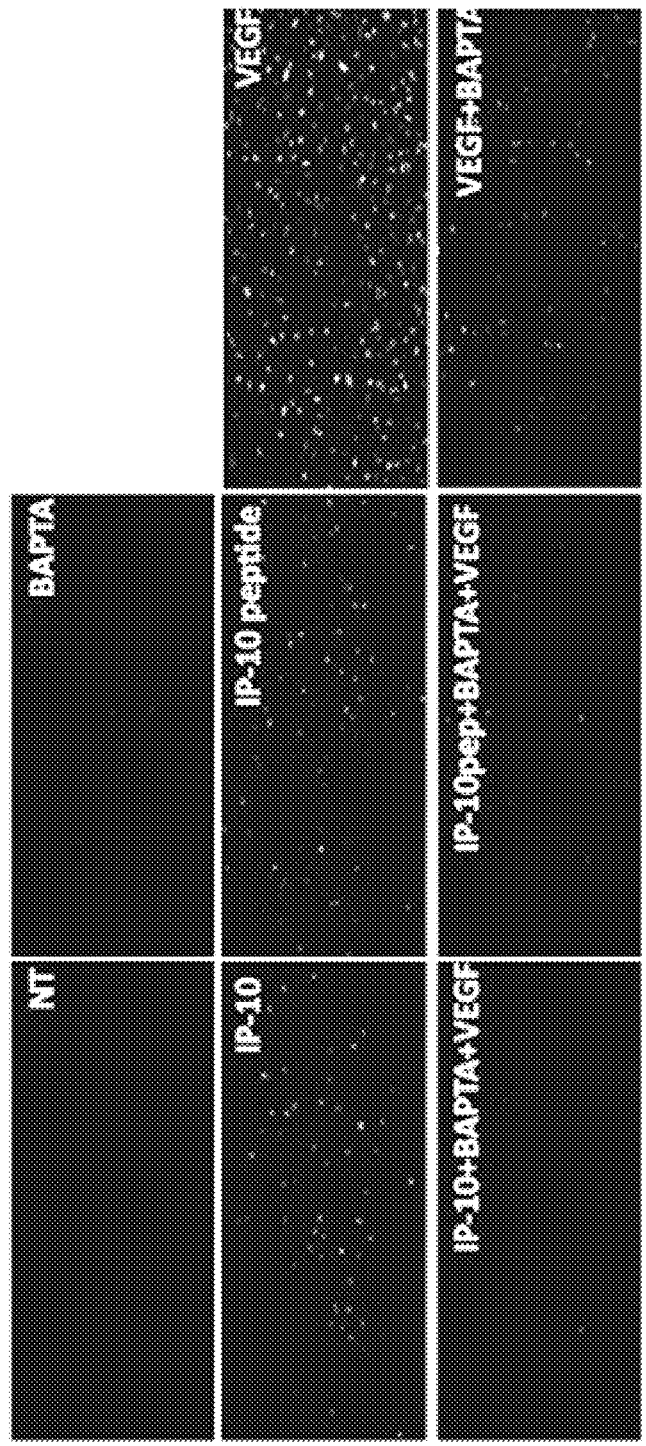
FIG. 7C is a grid of black and white photographs depicting fluorescence microscopy images at 10× magnification.
Figure 7D:
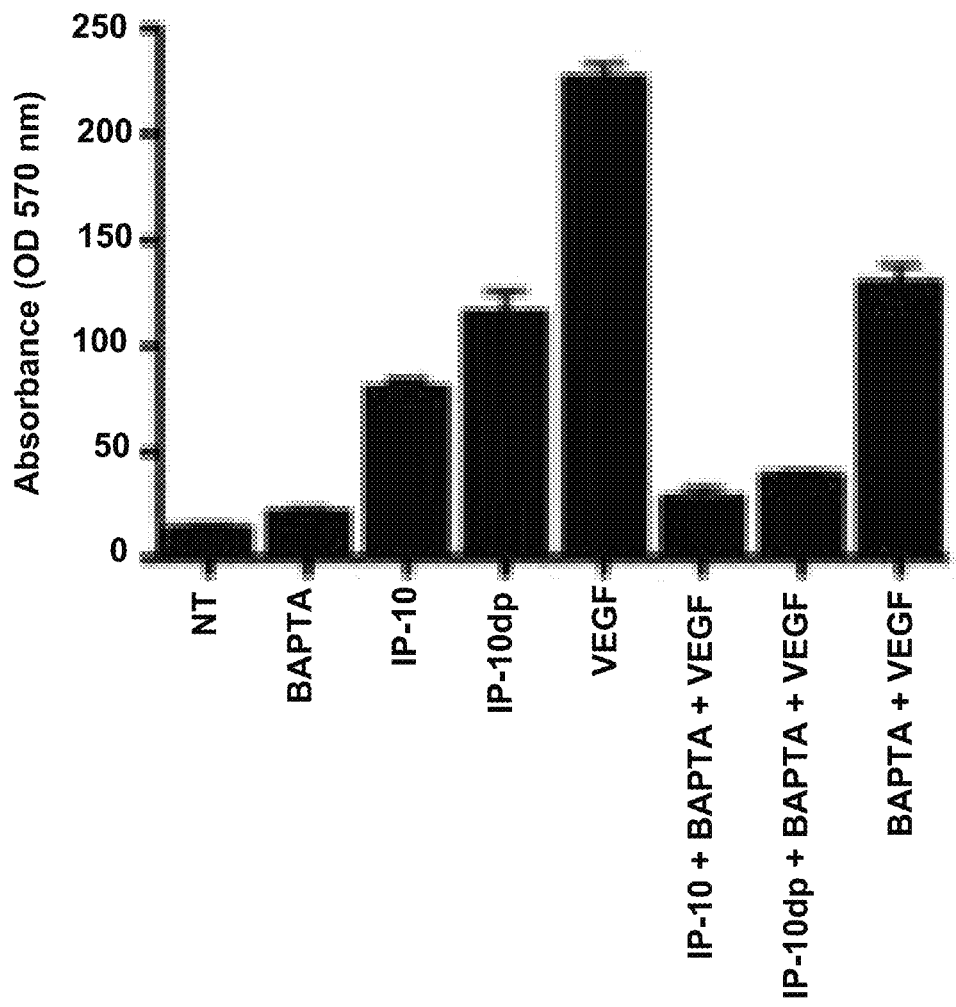
FIG. 7D is a graph comparing experimental results for tests measuring calpain activation of epithelial cells.

As shown by the images of the representative samples in FIG. 7C, when the cells were treated with VEGF and IP-10dp and/or IP-10, cleavage of Boc-LM-CMAC was observed. However, when the cells were pre-incubated with BAPTA/AM, which was similarly extinguished by IP-10 and IP-10dp, similar results were observed. Taken together these data suggest that the IP-10dp inhibits VEGF mediated m-calpain activity.

EXPERIMENT 11

The experiments above have demonstrated that IP-10dp is able to inhibit endothelial tube formation and induce the dissociation of formed tubes in vitro. To determine whether IP-10dp is able to inhibit vessel growth, an in vivo Matrigel assay was used to establish that IP-10dp is able to inhibit angiogenesis. Vessel development and regression in vivo was determined generally according to the method previously described by Bodnar et al. (see Bodnar et al., 2006, supra). In brief, for vessel development GFR Matrigel supplemented with $VEGF_{165}$ in the absence or presence of IP-10 or IP-10dp was injected into the groin area of the mice. Ten days post inoculation; the Matrigel plug was removed and stained with Masson Trichrome to visualize endothelial infiltration.

Specifically, Matrigel with VEGF was injected into the groin area near the dorsal midline of 12-month-old C57Bl/6 female mice. In addition to Matrigel plus VEGF, the mice were injected with saline (control), 10 μg of IP-10 or 100 μg of IP-10dp. Two injections were made in each mouse in separate dorsal areas, one control injection and the other with the designated experimental treatment. On day 10, the Matrigel plugs were removed and either paraffin embedded or flash frozen. They were prepared and examined histologically for new vessel development using Masson's trichrome staining. As shown in FIG. 8, the staining showed that VEGF induces endothelial invasion and formation of vessels (the top left photo is representative of a control sample of tissue that received only VEGF), yet the presence of either IP-10 (the top middle photo is representative of a test sample that received combined VEGF and IP-10 administration) or IP-10dp (the top right photo is representative of a test sample that received combined VEGF and IP-10 administration) inhibited this angiogenesis in the presence of VEGF. As can be seen from comparison of the images, however, the administration of IP-10dp appears to have been more effective than IP-10 in inhibiting VEGF-induced new vessel formation. This particular result is taken as being indicative that IP-10dp has the ability to inhibit VEGF-induced new vessel formation.

Further, to verify that IP-10dp is able to cause regression of newly formed vessels in vivo, parallel experiments were conducted on similar mice whereby GFR Matrigel supplemented with VEGF (200 ng/ml) was first injected into both the left and right side groins of mice (establishing a control location and a test location). After 10 days, the left side Matrigel plug was removed (control, n=6) and stained as above for histological examination, with the left side samples being used to establish the extent of new vessel invasion at 10 days. The remaining right side Matrigel plug in the mice was injected with either IP-10 (10 μg) or IP-10dp (100 μg) at days 10 and 12. Day 17, the right side Matrigel plugs were removed and stained for examination as above. FIG. 8D through FIG. 8G are color photographs of tissue samples, showing both 10× and 40× magnifications, taken from laboratory C57BL/6J mice. (See FIG. 8. On the top row, the photograph labeled as "VEGF" is referred to herein as "FIG.8A." The photograph labeled "IP-10" is referred to herein as "FIG.8B." The photograph labeled as "IP-10dp" is referred to herein as "FIG.8C." On the bottom row, the photograph labeled as "VEGF (Day 10)" is referred to herein as "FIG. 8D." The photograph labeled as "Saline (Day 17)" is referred to herein as "FIG. 8E." The photograph labeled as "IP-10 (day 17)" is referred to herein as "FIG.8F." The photograph labeled as "IP-10dp (Day 17)" is referred to herein as "FIG.8G."). Relative to control (FIG. 8D is a representative sample at day 10 showing the VEGF-induced vessels formed in the Matrigel plug, while FIG. 8E is a representative control sample at day 17 following saline administration), the samples that received IP-10dp (FIG. 8G is a representative test sample at day 17 following IP-10dp administration) showed a significant regression of vessels compared to the saline control. Tissue samples that received IP-10 administration (FIG. 8F is a representative test sample at day 17 following IP-10 administration) likewise showed a significant regression of vessels compared to control, however the regression observed was less than that observed for IP-10dp. These results also support a conclusion that IP-10dp causes the dissociation of, and subsequently the regression of, newly-formed vessels, similar in manner to IP-10.

In the various experiments above, the anti-angiogenic activity of the C-terminal peptide IP-10dp was examined. The experiments evidence that the peptide IP-10dp is able to inhibit angiogenesis and cause the regression of newly formed vessels, and thus that the α-helix region of IP-10 is the epitope that binds and signals via the CXCR3 receptor. The experiments also support a conclusion that IP1dap stimulation of microvascular endothelial cells promotes the activation of PKA by increasing levels of cAMP resulting in the inhibition of endothelial cell migration in a significant capacity comparable to the full length IP-10. Furthermore, the above experiments show that IP-10dp exerts a dominant affect on VEGF. Thus, the above experiments provide significant in vitro evidence supporting the efficacy of IP-10dp and peptides derived therefrom as therapeutics aimed at CXCR3 receptor.

EXPERIMENT 12

This experiments was performed to confirm the relationship of the CXCR3 ligands IP-10 and IP-10dp to later phase wound repair in mammals. A batch of C57BL/6J mice in which CXCR3 expression was abrogated were generated as described by Hancock et al. (Hancock et al., 2000, "Requirement of the chemokine receptor CXCR3 for acute allograft rejection. Journal of Experimental Medicine," 192(10), 1515-1520.). Wild type C57BL/6J were obtained from Jackson Laboratory.

Male and female mice (7-8 wk of age weighing approximately 25 g) were anesthetized with an intraperitoneal injection containing ketamine (75 mg/kg) and xylazine (5 mg/kg). The backs were cleaned, shaved, and treated with betadine solution. For full thickness wounds, sharp scissors were used to make an approximately 2 cm diameter full-thickness wound through the epidermis and dermis on one side of the dorsal midline; for comparison the dorsal length of the mice was about 7.5 cm long. The contralateral uninjured skin served as unwounded control skin. The wounds were covered with liquid occlusive dressing (New-Skin®, Medtech, and Jackson, Wyo.). This wounding assay was performed 3 independent times with at least four animals for each time.

To track and measure wound contraction, the animals were lightly anesthetized for several seconds. Wounds were traced onto a transparent sheet, at 2-day intervals until complete closure. Wound size was compared between the wild type and CXCR3−/− groups.

Additionally, wound bed biopsies surrounded by a margin of non-wounded skin were also collected at days 3, 5, 7, 14, 21, 30, 60, and 90 post-wounding. Wound biopsies were fixed in 10% buffered formalin, processed and embedded in paraffin blocks using standard protocols. Tissue sections (4 μm) were stained with hematoxylin and eosin and analyzed for general tissue and cellular morphology. Collagen deposits were evaluated by Masson's trichrome staining. For mouse tissue, paraffin sections of 4-5 μm were prepared for antibody staining. The following antibodies were used for immunohistochemical staining for mouse specimens: CXCR3 (rabbit polyclonal, R&D Systems), Fibronectin (rabbit polyclonal; Rockland), IP-10/CXCL10 (rabbit polyclonal, PeproTech), IP-9/CXCL11 (rabbit polyclonal, PeproTech), Tenascin C (rat polyclonal, R&D Systems), and Von Willebrand Factor (rabbit polyclonal, Abcam).

Histopathological examination of mouse tissues was performed blinded by a veterinary pathologist. Qualitative assessments were made concerning aspects of dermal and epidermal maturation, inflammation, and granulation tissue. The samples were scored on a scale of 0 to 4 for epidermal healing (0=no migration, 1=partial migration, 2=complete migration with partial keratinization, 3=complete keratinization, 4=normal epidermis) and dermal healing (0=no healing, 1=inflammatory infiltrate, 2=granulation tissue present—fibroplasias and angiogenesis, 3=collagen deposition replacing granulation tissue >50%, 4=complete healing). Quantification of fibroblastic hypercellularity was performed by using MetaMorph (Universal Imaging Corp).

The experimental results found differential expression of the CXCR3 ligands IP-9 and IP-10 during wound healing. IP-9 is expressed by keratinocytes just behind the leading edge of the wound and IP-10 is expressed deep in the dermis as well as at the wound edge in wild type mice. These same results are observed in the CXCR3−/− mice, suggesting that CXCR3 is not required for secretion of its ligands. While not significantly significant, it appeared possible that there was an increased ligand protein levels in the CXCR3 −/− mice potentially due to lack of receptor-mediated ligand attenuation.

EXPERIMENT 13

To assess the strength of newly formed regenerated wound tissue in terms of tensile strength, biopsies were wrapped flat in foil, snap frozen in liquid nitrogen, and then stored at −80° C. For the tensile strength measurements, the frozen specimens were divided into two samples, the cross-sectional area measured with calipers, and then the samples were clamped in a custom-built tensiometer and force exerted until wound disruption, as previously described (Sandulache et al., 2003). Measurements were recorded and tensile strength calculated using the formula: Maximum Tensiometer Reading (converted to g) divided by cross-sectional Area (mm2)=Tensile strength (g/mm$^2$). The results for individual specimens from one wound were combined to determine an average tensile strength per wound. The average tensile strength per wound was tabulated for each group at days 7, 14, 21, 30, 60 and 90 post-wounding.

A major function of the fibroplasia after wounding is to regenerate the collagen matrix of the dermis. However, it is only after the fibroblasts are channeled toward a 'differentiated' state that they become synthetic. Additionally, it has been speculated that myofibroblast contraction of the matrix is required for collagen bundling and alignment during the remodeling phase of wound repair. Thus, Applicants also investigated whether the CXCR3−/− mice presented a weakened dermis. Tensometry demonstrated that in unwounded skin, CXCR3−/− mice presented slightly higher tensile strength than wild type mice. However, during wound healing the regaining of tensile strength of the CXCR3−/− mice wounds lagged behind that of wild type mice, and even at 90 days after wounding, the CXCR3−/− mice regained only 40-50% of the prewounding strength compared to 70-80% for the wild type mice (FIG. 7A).

To determine whether this difference in regained tensile strength between the wild type and CXCR3−/− wounds is due to collagen content and organization, histological analyses were undertaken. Masson's trichrome staining showed less collagen in the CXCR3−/− wounds from days 7 through 90. In addition, the wild type wounds displayed a denser and more organized granulation tissue at day 90, suggesting better healing of these wounds. Picrosirius red staining showed that in the wounds of CXCR3−/− mice, the collagen fibers were short and the scar immature. Histological assessment of the hematoxylin and eosin-stained sections also detected an immaturity in the collagen of the dermal matrix. Notably, this collagen deficiency was not due to a paucity of fibroblasts; the CXCR3−/− mice presented a significantly hypercellular wound dermal compartment at day 90. This is consistent with CXCR3 activation being a 'stop immigration' signal. Interestingly, by day 90, when the wild type wounds were well past the regenerative stage, the CXCR3−/− wounds were still hyperkeratinized, hypercellular and contained a significantly greater density and/or number of blood vessels.

EXPERIMENT 14

This experiment was conducted to confirm whether the lack of CXCR3 in mice would delay normal dermal wound healing. In groups of normal wild type and CXCR3 −/− mice, 2 cm×2 cm full thickness wounds were made by removing the epidermal and dermal layers of the skin on the backs of mice. These wounds healed in both genotypes, but there was a greater than two day lag in the closure rate for the CXCR3−/− mice, with full closure occurring a week later on average. As full thickness wounds in mice are known to close predominantly via contraction, this delay was consistent with the in vitro mechanism of CXCR3 signaling channeling dermal fibroblasts from migration to contraction.

The delay in full thickness wound healing was evident by day 7 in the CXCR3−/− mice compared to the wild type mice. However, after an extended time period, the abnormality in healing of full thickness wounds became more apparent to the naked eye. Even after three months, the CXCR3−/− mice wounds presented what appeared to be a scab, due to its flaky appearance. Histological examination of these day 21 to 90 wounds revealed a thicker epithelial layer and prominent thick and hypercellular stratum corneum (hyperkeratinization), seemingly less well connected to the dermis late as day 90. Histological examination of the biopsies presented an immature hypercellular dermis and supported the conclusion that CXCR3 signaling serves as an "off" signal for wound healing and helps to trigger the final phase of wound healing, wound resolution.

The exuberant cellularity that marks the regenerative phase is reversed during the wound resolution phase of healing. Thus, the noted hypercellularity in the CXCR3 −/− mice noted in this Experiment months after wounding and even wound closure was interpreted by Applicants as evidence of a deficit in this regression. The tissue samples were also probed for a marker of apoptotic cell death, free ends indicative of DNA fragmentation in these wounds. TUNEL staining of the wound field biopsies demonstrated that 30 and 60 days after wound healing, there was a significantly greater absolute and relative number of apoptotic cells in the dermis in the wounds of wild-type mice compared with CXCR3−/− mice. However, by day 90, at which time point the healed wounds in wild-type mice are paucicellular, dermal cell apoptosis continued in the wound fields of the CXCR3−/− mice. This finding was interpreted by Applicants as suggesting that the CXCR3 signaling of IP-9 and IP-10 is at least in part responsible for the cell apoptosis during the resolving phase that restores a paucicellular dermis.

One of the defining aspects of mature skin is the maturation of the matrix to allow for a basement membrane delineating the dermal-epidermal separation. This transition from immature matrix to delineating margin is marked by progression from expression of fibronectin and tenascin-C to laminin V and collagen IV by both dermal fibroblasts and epithelial keratinocytes. In the CXCR3 −/− mice, it was found that the progression to a mature matrix and a remodeled basement membrane appeared retarded. Staining for provisional matrix components tenascin-C and fibronectin showed a persistence of the transient tenascin-C and the reactive fibronectin expression at 90 days both throughout the dermis and in the area that should form the basement membrane barrier in the CXCR3−/− wounds.

EXPERIMENT 15

A parallel experiment to Experiment 12 was conducted in human subjects. For each subject, full-thickness 6 mm (open) wounds were made in the skin of the hip region of healthy young adult human volunteers and biopsies taken on days 0, 2, 4, 14 and 28 post-wounding. Paraffin tissue sections (5 μm) were stained with hematoxylin and eosin for morphological observations. Sections for immunohistochemical analysis were incubated with appropriately diluted primary antibody, after antigen retrieval (BioGenex, SanRamon, Calif.). Antigen staining was performed using DAB (Vector Laboratories, Burlingame, Calif.), then counterstained with Mayer's hematoxylin and coverslipped. In all cases, secondary antibody alone served as a negative control, with various human tumor tissues serving as positive controls.

For staining of the human specimens, the following primary antibodies were used: CXCR3 (rabbit polyclonal, R&D Systems), IP-9/CXCL11 (goat polyclonal, Santa Cruz), and IP-10/CXCL10 (goat polyclonal, Santa Cruz). Analysis found that during the healing process in human wounds, IP-9 is expressed during the early granulation phase and IP-10 in the late granulation/early resolving phase. The results demonstrated a good correlation in IP-9 and IP-10 expression between mouse and human during the wound healing process.

EXPERIMENT 16

This experiment was conducted to determine the impact of CXCR3 ligand chemokine presence or absence on wound healing characteristics in a FVB mice model. The pathophysiological effects of the suppression of IP-9 during healing were determined by creating full and partial thickness excisional wounds in the dorsal skin on the IP-9AS and FVB (wild type) mice. Briefly, the antisense construct was generated by cloning the IP-9 cDNA into the SnaB1 site of the pBK5 vector, which contains 5.2 kb of the bovine cytokeratin K5 promoter. After verification that this construct could significantly blunt the interferon-γ induction of IP-9 in human keratinocytes, this was used to generate transgenic mice. Founders were identified by germline transmission of the transgene using PCR of tail clip DNA (forward: 5'-CAT ATG AAG TCC TGG AAA AGG G-3' (SEQ ID NO: 4); reverse: 5'-ACA ACT ACA CCC TGG TCA TCA-3') (SEQ ID NO: 5)). Mice sibmated by transgene x wildtype. The transgenic mice are referred to IP-9AS. In the transgene, IP-9 production was not noted during wound repair.

From this animal population, male and female mice (7-8 wk of age weighing approximately 25 g) were anesthetized with an intraperitoneal injection containing ketamine (75 mg/kg) and xylazine (5 mg/kg). The backs were cleaned and shaved and sterilized with betadine solution. For full thickness wounds, a 2 cm full-thickness wound through the epidermis and dermis was made on one side of the dorsal midline, using sharp scissors, with the contralateral uninjured skin serving as a control. Partial thickness wounds were made with a specially-modified dermatome. The wounds were covered with liquid occlusive dressing (New-Skin®, Medtech, Jackson, Wyo.). This experiment was performed in duplicate.

To follow the wound progression visually, the animals were lightly anesthetized for several seconds with a halothane cone. A transparent sheet was placed over the wound. Re-epithelialization of the wound was traced at 2-day intervals until complete closure. These parameters were compared between the wild type and IP-9AS.

Wound bed biopsies, including a margin of non-wounded skin, were collected at days 5, 7, 14, 21, 30, and 60 post-wounding. Wound biopsies were fixed in 10% buffered formalin, processed and embedded in paraffin blocks using standard protocols. Four-μm tissue sections were stained with hematoxylin and eosin (H&E) for assessment of general tissue and cellular morphology. Collagen deposition, content, and alignment were evaluated by Masson's Trichrome and Picrosirius Red staining. Slides were quantitatively analyzed using MetaMorph (Universal Imaging Corp).

The histological scoring system was developed based on the Greenhalgh scoring system. For acute inflammation, it was defined as the presence of neutrophils and chronic inflammation by the presence of plasma and monocytic cells (0, none; 1, slight; 2, moderate; 3, abundant). In both situations the scale was secondary to relative level of cells per high power field. For eidermal and dermal maturation, histopathological examination of mouse tissues was performed blinded by a trained histo-pathologist and qualitative assessments were made concerning aspects of dermal and epidermal maturation, inflammation, and granulation tissue. The samples were scored on a scale of 0 to 4 for epidermal healing (0, no migration; 1, partial migration; 2, complete migration with partial keratinization; 3, complete keratinization; and 4, normal epidermis) and dermal healing (0, no healing; 1, inflammatory infiltrate; 2, granulation tissue present—fibroplasias and angiogenesis; 3, collagen deposition replacing granulation tissue >50%; and 4, complete healing).

Further, Masson's trichrome staining was used to assess collagen content using MetaMorph analysis (Molecular Devices). Stained wound biopsies were compared with that of the unwounded controls: at all times the colors was maintained to compare the blue- and red-stained areas. The final output was integrated intensity based on total area and staining intensity at individual pixels. All wound biopsies were stained at the same time to eliminate staining variation.

Picrosirius red staining was used to assess collagen alignment and organization in intact biopsies. Briefly, picric acid (Sigma-Aldrich, St. Louis, Mo.) was dissolved in 500 ml of distilled water. To this, 0.1 g of Sirius red F3BA was added per 100 ml (Sigma-Aldrich). Paraffin-embedded tissue sections were rehydrated and stained with picric acid. Collagen fibrils were then evaluated by means of polarized light microscopy for both collagen fibril thickness and coherence alignment. Polarization microscopy reveals closely packed thick fibrils of type I collagen fibers as either red-orange intense birefringence in the hypertropic tissue, with thin short loose fibrils as yellow-green. Distribution of fibrils in terms of thickness (cross-sectional area) and arrangement in terms of length of the collagen scars were quantitatively analyzed using Meta-Morph (Molecular Devices). Biopsies of unwounded skin served to set the threshold against which the wound biopsies were measured. Percent staining of mature fibers was determined by comparing the total staining intensity of the birefringence (area of staining summed for intensity of pixel) of wound biopsies compared with the biopsies of the contralateral unwounded skin.

Sections for immunohistochemical analysis were incubated with appropriately diluted primary antibody, after antigen retrieval. Antigen staining was performed using diaminobenzidine (Vector Laboratories, Burlingame, Calif.), then counterstained with Mayer's hematoxylin and coverslipped. In all cases, secondary antibody alone served as a negative control, with various tissues serving as positive controls. Paraffin sections of 4 to 5 μm were prepared for antibody staining. The following antibodies were used for immunohistochemical staining for mouse: Fibronectin (rabbit polyclonal; Rockland, Inc., Gilbertsville, Pa.), IP-9 (goat polyclonal; Santa Cruz Biotechnology, Santa Cruz, Calif.), tenascin-C (rat polyclonal; R&D Systems), Collagen IV (rabbit polyclonal; Abcam Inc., Cambridge, Mass.), Ki67 (rabbit polyclonal; Abcam Inc., Cambridge, Mass.).

For this experiment, a delay in healing was observed in the IP-9AS mice with the eschar being present at least 14 days longer than in the wild type mice. In the full thickness wounds, the gross deficits were more subtle. This was not unexpected as full thickness skin wounds in rodents close mainly by contraction, while deep in the dermis CXCL10/IP-10 appears to be the predominant CXCR3 ligand.

Analyzed histologically, the wounds in the IP-9AS mice showed both a delayed re-epithelialization and an immature epidermis. In partial thickness wounds, the progressing keratinocyte tongue was delayed, and even where the underlying dermis was covered, the epidermal layer was thicker with more transit amplifying cells even as long as 30 days after wounding at which time the wounds in wild type mice appear fully healed. This correlates with the corresponding increase in the number of cell layers that constitute the epidermis in the IP-9AS wounds (0.0202 mm in IP-9AS vs. 0.0080 mm in the FVB mice).

The late-stage wounds in the wild type mice resemble that of normal skin with a low number of keratinocytes presenting the proliferation marker Ki67, while a greater number of nuclei stain positive for Ki67 as late a 30 days post-injury in the IP-9AS mice. This suggests a degree of wound retardation or immaturity in these mice. Epidermal maturation is also deficient in the full thickness wounds, showing that this maturation aspect is independent of actual wound edge juxtapositioning. The number of cell layers also increased in IP-9AS full-thickness wounds.

Fibroplasia and epithelialization, two distant aspects of skin healing, also both appeared to be impacted by CXCR3 signaling in this Experiment. Even in full thickness wounds, dermal maturation was delayed up to 60 days post-wounding. Masson trichrome staining for collagen content shows a clear morphological difference in the dermal matrix with the wounds in IP-9AS mice having less deposited collagen and greater fibroblast cellularity in comparison to wounds in FVB control mice. Quantification of the dermal wounds revealed that IP-9AS mice failed to properly remodel the dermal matrix as late as day 60 post wounding. Picrosirius red staining showed that the IP-9AS wounds had shorter and less well connected collagen fibers resulting in a less well organize with respect to regain of tensile strength and immature scar. Consistent with this collagen immaturity, provisional matrix components including tenascin C and fibronectin are delayed in appearance and persist longer in the wounds of IP-9AS mice.

In the partial thickness wounds, the superficial, papillary dermis was removed by the dermatome (Hebda, Klingbeil, Abraham, & Fiddes). In this region, dermal repair was deficient in IP-9AS wounds, showing collagen and matrix immaturity. Importantly for skin healing, the delineating basement membrane between the dermal and epidermal compartments was deficient. Most obvious, is the elevated expression of collagen IV (FIG. 14) in the late healing phase of the IP-9AS mice suggesting that the epidermis-dermal junction has yet to properly form, resulting in a looser connection between these layers in the healed wounds of the IP-9AS mice (FIG. 12B).

EXPERIMENT 17

For the mice of Experiment 16, tensile strength of the biopsies was analyzed because it is well documented that tensile properties of a wound depend not only on the amount of collagen, but also on the organization and crosslinking of the matrix. Biopsies obtained from the mice of Experiment 16 were wrapped flat in foil, snap frozen in liquid nitrogen, and then stored at −80° C. For the tensile strength measurements, the frozen specimens were divided into two samples, the cross-sectional area measured with calipers, and then the samples were clamped in a tensiometer and force exerted until wound disruption, as previously described (Hebda et al.) The tensiometer was calibrated after every third sample with a wide range of weights. Measurements were recorded by a customized computer software program and tensile strength calculated using the formula: Maximum Tensiometer Reading (converted to g) divided by Cross-sectional Area (mm2)= Tensile strength (g/mm2). The results for individual specimens from one wound were combined to determine an average tensile strength per wound. The average tensile strength per wound was tabulated for each group at days 7, 14, 21, 30, and 60 post wounding.

Tensiometry demonstrated that IP-9AS mice wounds lagged behind those of the control mice with respect to regain of tensile strength; even at 60 days after wounding, the IP-9AS mice regained only 60 to 65% of the prewounding strength compared to the 75 to 80% for the control mice. These results suggest that not only does chemokine IP-9 affect epidermal healing but dermal healing as well by contributing to fibroblast immigration, collagen bundling and alignment, and dermal strength (collagen organization).

The various experiments outlined above confirmed through both in vitro and in vivo data that CXCR3 ligand chemokines such as IP-9 and IP-10 are notable in wound healing and in inhibiting angiogenesis, and that IP-10dp has similar CXCR3 signaling properties to IP-10. While being significantly smaller than IP-10, the data suggests that IP-10dp is bioactively comparable to, if not superior to, full length IP-10. Thus, one skilled in the art will appreciate that IP-10dp and peptides derived therefrom may be used advantageously as therapeutics for anti-angiogenic treatments and chronic wound therapies because of its small size and inhibitory abilities even at low doses. Since IP-10dp is a small active fragment, its bioavailability and therapeutic value may be enhanced through its combined use with engineered agents, (e.g., relatively small fusion proteins containing the sequence IP-10dp) or in nanotechnology-directed therapies.

Having described preferred embodiments of the invention, it will now become apparent to those of ordinary skill in the art that other embodiments incorporating these concepts may be used. Accordingly, it is submitted that that the invention should not be limited to the described embodiments but rather should be limited only by the spirit and scope of the appended claims.

Thus, although the invention has been described and illustrated with a certain degree of particularity, it is understood that the present disclosure has been made only by way of example, and that numerous changes in the combination and arrangement of steps, ingredients, or processes can be resorted to by those skilled in the art without departing from the spirit and scope of the invention, as will be claimed.

---

BIOSEQUENCES

SEQ. ID NO. 1 - IP-10dp
PESKAIKNLLKAVSKEMSKRSP

SEQ. ID NO. 2 - IP-10
VPLSRTVRCTCISISNQPVNPRSLEKLEIIPASQFSPRVEIIATMKKKG
EKRCLNPESKAIKNLLKAVSKEMSKRSP

SEQ. ID NO. 3 - IP-9
MSVKGMAIALAVILCATVVQGFPMFKRGRCLCIGPGVKAVKVADIEKAS
IMYPSNNCDKIEVIITLKENKGQRCLNPKSKQARLIIKKVERKNF

---

The invention claimed is:

1. A method for inhibiting endothelial cell motility, vessel formation and inducing vessel dissociation in a mammal diagnosed as having a chronic wound, comprising administering to the mammal an effective amount of a compound comprising a peptide that is at least 95% identical to the peptide of SEQ ID NO: 1; wherein said peptide binds with and activates chemokine receptor CXCR3 and wherein said activation of the chemokine receptor CXCR3 inhibits endothelial cell motility and vessel formation and induces vessel dissociation; and wherein the compound is applied to said chronic wound in the form of a topical formulation having said compound in a topical carrier; and wherein said topical formulation comprises two or more compounds that are ligands of chemokine receptor CXCR3.

2. The method according to claim 1, wherein said peptide is SEQ ID NO: 1.

3. A method for mediating regression of vascular vessels to inhibit angiogenisis in a mammal diagnosed as having a chronic wound, said method comprising administering to a mammal an effective amount of a compound comprising a peptide that is at least 95% identical to the peptide of SEQ ID NO:1; and wherein said peptide binds with and activates chemokine receptor CXCR3 and wherein said activation with the chemokine receptor CXCR3 mediates regression of vascular vessels to inhibit angiogenesis; and wherein the compound is applied to said chronic wound in the form of a topical formulation having said compound in a topical carrier; and wherein said topical formulation comprises two or more compounds that are ligands of chemokine receptor CXCR3.

4. The method according to claim 3, wherein said peptide is SEQ ID NO: 1.

* * * * *